United States Patent
Rifkin

(10) Patent No.: US 8,821,589 B2
(45) Date of Patent: Sep. 2, 2014

(54) JOINTS FOR PROSTHETIC, ORTHOTIC AND/OR ROBOTIC DEVICES

(76) Inventor: Jerome R. Rifkin, Louisville, CO (US)

(*) Notice: Subject to any disclaimer, the term of this patent is extended or adjusted under 35 U.S.C. 154(b) by 161 days.

(21) Appl. No.: 12/464,747

(22) Filed: May 12, 2009

(65) Prior Publication Data

US 2009/0287314 A1 Nov. 19, 2009

Related U.S. Application Data

(60) Provisional application No. 61/127,482, filed on May 13, 2008.

(51) Int. Cl.
*A61F 2/68* (2006.01)
*A61F 2/66* (2006.01)
*A61F 2/50* (2006.01)
*A61F 2/30* (2006.01)

(52) U.S. Cl.
CPC ........... *A61F 2/66* (2013.01); *A61F 2220/0033* (2013.01); *A61F 2002/5093* (2013.01); *A61F 2310/00047* (2013.01); *A61F 2002/30359* (2013.01); *A61F 2002/6621* (2013.01); *A61F 2/6607* (2013.01); *A61F 2002/6642* (2013.01); *A61F 2002/6635* (2013.01); *A61F 2310/00017* (2013.01); *A61F 2002/30462* (2013.01); *A61F 2002/5041* (2013.01); *A61F 2220/0075* (2013.01)
USPC ..................... 623/53; 623/54; 623/55; 623/51

(58) Field of Classification Search
USPC ...................................... 623/53, 51
See application file for complete search history.

(56) References Cited

U.S. PATENT DOCUMENTS

| | | | | |
|---|---|---|---|---|
| 78,048 | A | * | 5/1868 | Briody ............................ 623/50 |
| 197,943 | A | | 12/1877 | Osborne |
| 469,348 | A | | 2/1892 | Kane |
| 556,201 | A | | 3/1896 | Neubert |
| 710,996 | A | | 10/1902 | Peer |

(Continued)

FOREIGN PATENT DOCUMENTS

| CN | 2817775 | 9/2006 |
|---|---|---|
| DE | 309 066 C | 11/1917 |

(Continued)

OTHER PUBLICATIONS

U.S. Appl. No. 12/630,934, filed Dec. 4, 2009, Rifkin.

(Continued)

*Primary Examiner* — David Isabella
*Assistant Examiner* — Jacqueline Woznicki
(74) *Attorney, Agent, or Firm* — Leyendecker & Lemire, LLC

(57) ABSTRACT

An artificial foot device may include a core, a talus body operatively coupled with the core by a first joint, and a toe operatively coupled with the core by a second joint. The first joint may provides for constrained relative movement between the talus body and the core. The second joint may provide for constrained relative movement between the core and the toe. In some embodiments, the core may include a core assembly including a core body, an Achilles sheave coupled with the core body and a toe bracket coupled with the core body. The toe bracket may be operatively coupled with the toe, and the Achilles sheave may be operatively coupled with the talus body. Constrained relative movement between the talus body and the core may substantially correspond to a coordinated movement of a first natural joint and a second natural joint during ambulation of a natural human foot.

34 Claims, 38 Drawing Sheets

(56) References Cited

U.S. PATENT DOCUMENTS

| | | | |
|---|---|---|---|
| 809,875 A | 1/1906 | Wilkins | |
| 1,289,580 A | 12/1918 | Vincenti | |
| 2,098,067 A | 11/1937 | Simonsson | |
| 2,215,525 A | 9/1940 | Jeter | |
| 2,252,206 A | 8/1941 | Rice | |
| 2,439,195 A | 4/1948 | Witmyer et al. | |
| 2,475,372 A | 7/1949 | Catranis | |
| 2,475,373 A | 7/1949 | Catranis | |
| 2,483,506 A | 10/1949 | Sartin | |
| 2,620,485 A | 12/1952 | Greissinger | |
| 2,644,165 A | 7/1953 | Grisoni | |
| 2,692,392 A | 10/1954 | Bennington et al. | |
| 2,692,990 A | 11/1954 | Schaefer | |
| 3,196,463 A | 7/1965 | Farneth | |
| 4,267,608 A | 5/1981 | Bora, Jr. | |
| 4,499,613 A | 2/1985 | Yarrow | |
| 4,652,266 A | 3/1987 | Truesdell | |
| 4,717,288 A | 1/1988 | Finn et al. | |
| 4,892,554 A | 1/1990 | Robinson | |
| 4,932,806 A | 6/1990 | Eklund et al. | |
| 5,139,525 A * | 8/1992 | Kristinsson | 623/55 |
| 5,258,038 A | 11/1993 | Robinson et al. | |
| 5,376,139 A * | 12/1994 | Pitkin | 623/51 |
| 5,425,780 A | 6/1995 | Flatt et al. | |
| 5,439,060 A | 8/1995 | Huete et al. | |
| 5,443,522 A | 8/1995 | Hiemisch | |
| 5,443,527 A | 8/1995 | Wilson | |
| 5,482,513 A | 1/1996 | Wilson | |
| 5,507,838 A | 4/1996 | Chen | |
| 5,545,234 A | 8/1996 | Collier, Jr. | |
| 5,571,210 A * | 11/1996 | Lindh | 623/38 |
| 5,571,212 A | 11/1996 | Cornelius | |
| 5,695,526 A | 12/1997 | Wilson | |
| 5,725,598 A | 3/1998 | Phillips | |
| 5,766,264 A | 6/1998 | Lundt | |
| 5,826,304 A | 10/1998 | Carlson | |
| 5,913,902 A | 6/1999 | Geible | |
| 5,957,981 A | 9/1999 | Garmnas | |
| 5,993,487 A | 11/1999 | Skardoutos et al. | |
| 6,007,582 A | 12/1999 | May | |
| 6,019,795 A | 2/2000 | Phillips | |
| 6,099,572 A | 8/2000 | Mosler et al. | |
| D431,654 S | 10/2000 | Cruz | |
| 6,165,228 A | 12/2000 | Lindh | |
| 6,187,052 B1 | 2/2001 | Molino et al. | |
| 6,197,066 B1 | 3/2001 | Gabourie | |
| 6,197,068 B1 | 3/2001 | Christensen | |
| 6,206,934 B1 | 3/2001 | Phillips | |
| 6,238,437 B1 | 5/2001 | Johnson et al. | |
| 6,290,730 B1 | 9/2001 | Pitkin et al. | |
| 6,443,995 B1 | 9/2002 | Townsend et al. | |
| 6,669,737 B2 | 12/2003 | Mosler et al. | |
| 6,699,295 B2 | 3/2004 | Lee et al. | |
| 6,702,860 B1 | 3/2004 | Laghi | |
| 6,712,860 B2 | 3/2004 | Rubie et al. | |
| 6,743,260 B2 | 6/2004 | Townsend et al. | |
| 6,764,521 B2 | 7/2004 | Molino et al. | |
| 6,936,074 B2 | 8/2005 | Townsend et al. | |
| 7,112,227 B2 | 9/2006 | Doddroe et al. | |
| 7,563,288 B2 | 7/2009 | Doddroe et al. | |
| 7,833,287 B2 | 11/2010 | Doddroe et al. | |
| 7,862,621 B2 | 1/2011 | Kloos et al. | |
| 8,480,760 B2 | 7/2013 | Hansen et al. | |
| 2004/0064195 A1 | 4/2004 | Herr | |
| 2004/0243253 A1* | 12/2004 | Cool et al. | 623/52 |
| 2005/0216097 A1 | 9/2005 | Rifkin | |
| 2007/0061016 A1 | 3/2007 | Kuo et al. | |
| 2007/0255427 A1 | 11/2007 | Kloos et al. | |
| 2011/0015762 A1 | 1/2011 | Rifkin | |
| 2011/0093091 A1 | 4/2011 | Rifkin | |
| 2011/0208322 A1 | 8/2011 | Rifkin | |

FOREIGN PATENT DOCUMENTS

| | | |
|---|---|---|
| DE | 326131 | 9/1920 |
| DE | 365457 | 12/1922 |
| DE | 3239959 | 5/1984 |
| DE | 10010302 | 9/2001 |
| EP | 0940129 | 9/1999 |
| FR | 25322 | 1/1923 |
| FR | 2293186 | 7/1976 |
| GB | 1092 | 0/1858 |
| RU | 2092135 | 10/1997 |
| SU | 1409258 | 7/1988 |
| WO | WO 89/05617 | 6/1989 |
| WO | WO 91/06260 | 5/1991 |
| WO | WO 98/53769 | 12/1998 |
| WO | 01/49221 A1 | 7/2001 |
| WO | WO 03/013401 A1 | 2/2003 |

OTHER PUBLICATIONS

Preliminary Amendment dated Jul. 14, 2010, U.S. Appl. No. 12/630,934, 7 pages.
Office Action dated Apr. 12, 2012, U.S. Appl. No. 12/630,934, 8 pages.
Preliminary Amendment dated Oct. 13, 2010, U.S. Appl. No. 12/903,803, 6 pages.
Preliminary Amendment dated Jan. 3, 2011, U.S. Appl. No. 12/903,803, 6 pages.
Preliminary Amendment dated Nov. 2, 2005, U.S. Appl. No. 11/080,972, 11 pages.
Restriction Requirement dated Sep. 26, 2008, U.S. Appl. No. 11/080,972, 5 pages.
Response to Restriction Requirement dated Feb. 18, 2009, U.S. Appl. No. 11/080,972, 8 pages.
Notice of Non-Compliant Amendment dated Apr. 30, 2009, U.S. Appl. No. 11/080,972, 3 pages.
Amendment and Response to Notice of Non-Compliant Amendment dated May 15, 2009, U.S. Appl. No. 11/080,972, 8 pages.
Notice of Non-Compliant Amendment dated Aug. 7, 2009, U.S. Appl. No. 11/080,972, 3 pages.
Amendment and Response to Notice of Non-Compliant Amendment dated Aug. 28, 2009, U.S. Appl. No. 11/080,972, 10 pages.
Office Action dated Sep. 25, 2009, U.S. Appl. No. 11/080,972, 12 pages.
Amendment and Response to Office Action dated Feb. 25, 2010, U.S. Appl. No. 11/080,972, 12 pages.
Final Office Action dated Apr. 15, 2010, U.S. Appl. No. 11/080,972, 13 pages.
Office Action dated Feb. 4, 2013, U.S. Appl. No. 13/031,054, 6 pages.
Amendment and Response to Office Action dated Aug. 5, 2013, U.S. Appl. No. 13/031,054, 11 pages.
Final Office Action dated Jan. 2, 2013, U.S. Appl. No. 12/630,934, 8 pages.
Request for Continued Examination and Amendment and Response to Final Office Action dated Jul. 2, 2013, U.S. Appl. No. 12/630,934, 13 pages.
Final Office Action dated Aug. 2, 2013, U.S. Appl. No. 12/630,934, 5 pages.
Amendment and Response to Office Action dated Nov. 8, 2012, U.S. Appl. No. 12/903,803, 12 pages.
Final Office Action dated Jan. 22, 2013, U.S. Appl. No. 12/903,803, 9 pages.
Request for Continued Examination and Amendment and Response to Final Office Action filed Jul. 22, 2013, U.S. Appl. No. 12/903,803, 15 pages.
Amendment and Response to Office Action dated Oct. 12, 2012, U.S. Appl. No. 12/630,934, 16 pages.
Office Action dated May 8, 2012, U.S. Appl. No. 12/903,803, 8 pages.
Response to Final Office, RCE dated Jan. 31, 2014, U.S. Appl. No. 12/630,934, 10 pages.
Final Office Action dated Aug. 23, 2013, U.S. Appl. No. 12/903,803, 6 pages.
Final Office Action date Oct. 11, 2013, U.S. Appl. No. 13/031,054, 6 pages.

* cited by examiner

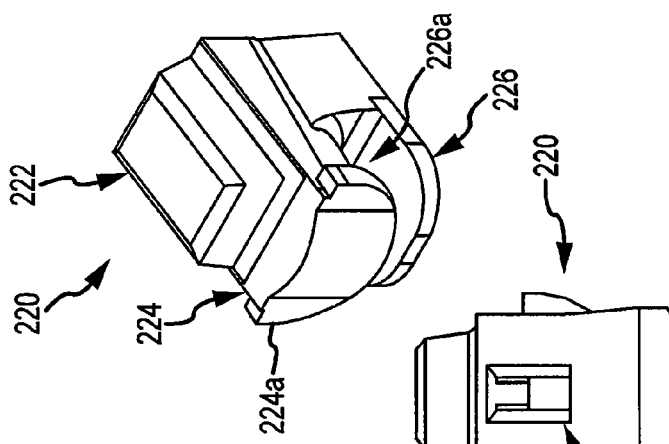
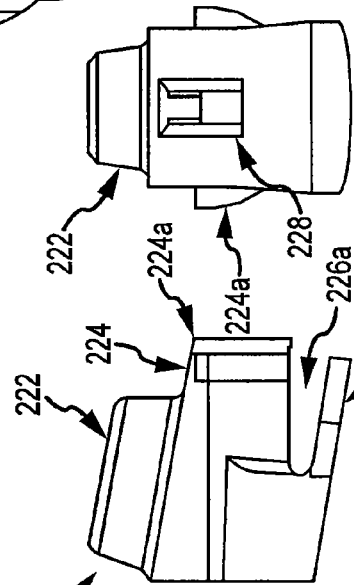
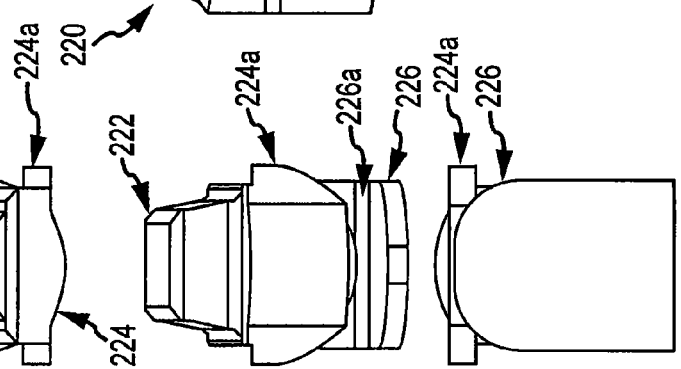

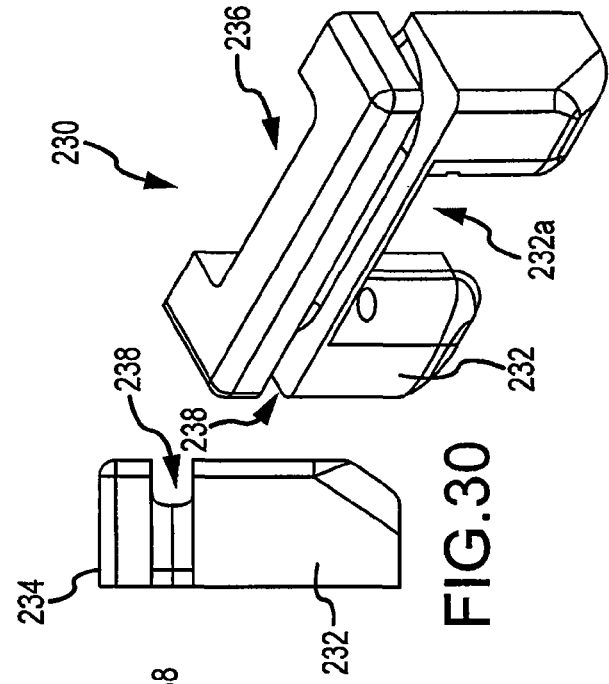
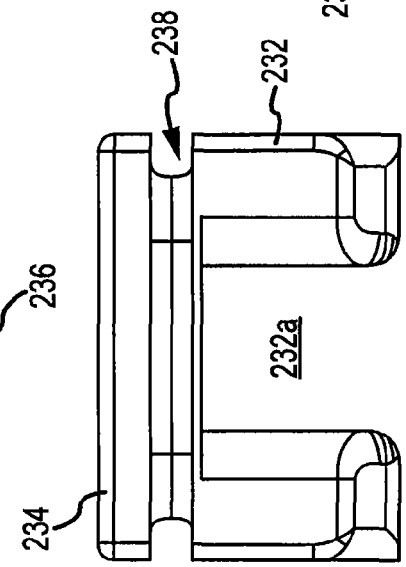
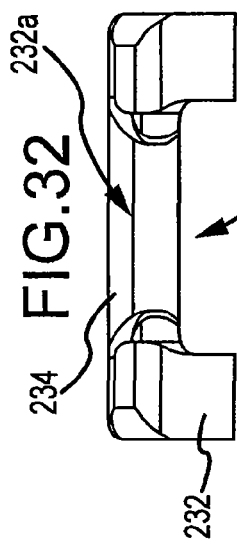
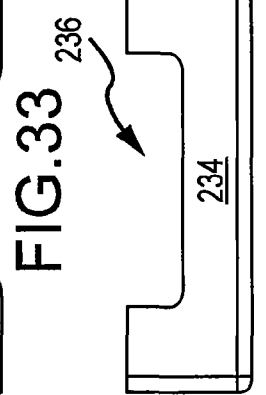

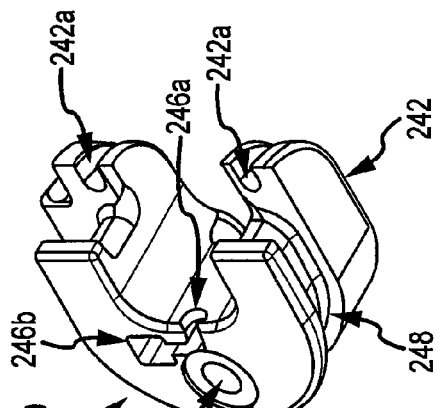
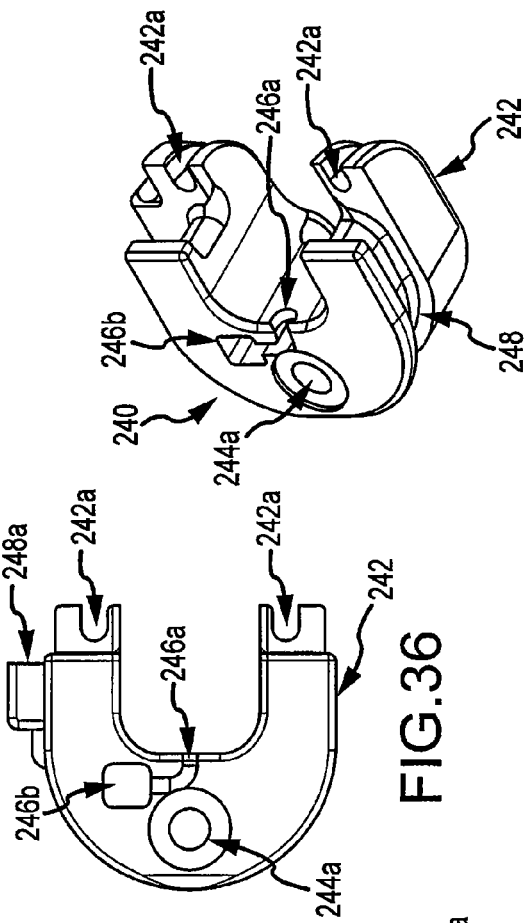
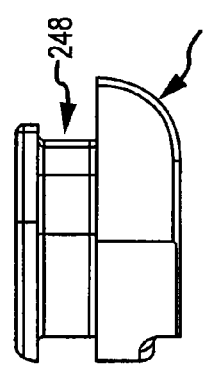
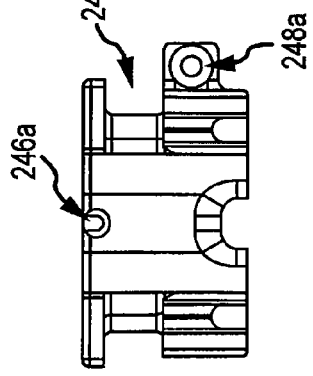
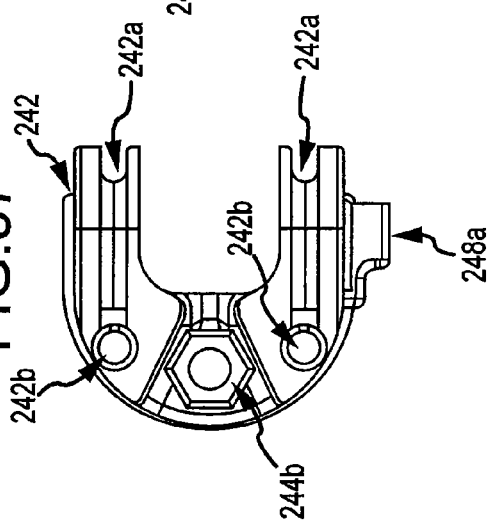

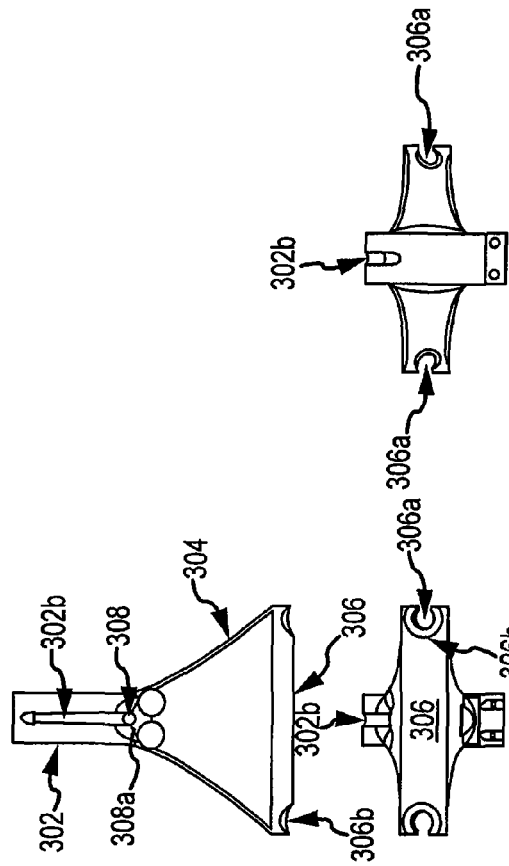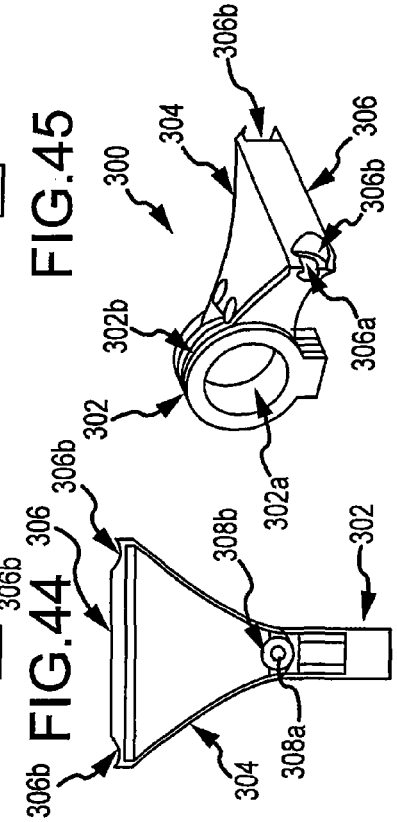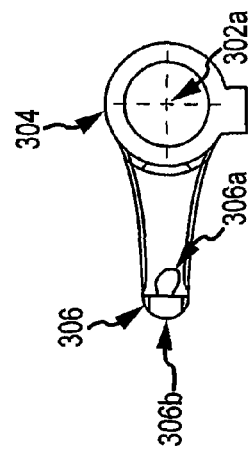

JOINTS FOR PROSTHETIC, ORTHOTIC AND/OR ROBOTIC DEVICES

REFERENCE TO RELATED APPLICATIONS

This application is related to pending U.S. patent application Ser. No. 11/080,972, filed Mar. 16, 2005, which claims the benefit of priority of provisional U.S. Patent Application No. 60/553,619, filed Mar. 16, 2004, the entirety of which are incorporated herein by reference.

This application claims the benefit of priority of provisional U.S. Patent Application No. 61/127,482, filed May 13, 2008, the entirety of which is incorporated herein by reference.

TECHNICAL FIELD

This application relates generally to artificial foot devices, such as a prosthetic, orthotic or robotic foot that simulates the coordinated motions of the natural human foot, particularly in walking gait. More particularly, embodiments of this application relate to a prosthetic, orthotic or robotic foot including three segments connected by two joints: one joint analogous to the human first metatarsophalangeal joint, and the other joint analogous to the human subtalar joint.

BACKGROUND

People who lose a leg today may be in a bad situation. Some days, a simple staircase may seem like an insurmountable challenge. Walking up a grassy slope is too difficult to attempt, because multiple falls may be inevitable. War, accidents and disease keep this disadvantaged population growing. Prosthetics, or synthetic replacements for missing anatomical structures, hold the promise of restoring some of this lost function and improving quality of life.

Just trying to regain functional mobility, amputees spend an average of $8,000 on below-knee (BK) prosthetic legs that last three to five years. Rather than spend this money on costly, non-repairable devices, one hundred and twenty thousand American amputees have chosen crutches or wheelchairs, and they won't walk again.

Just as the speed of a vehicle is maintained through regular energetic pushes received from pistons firing in the engine, normal human gait relies on well-timed pushes from the anatomy of the foot, during the toe-off portion of the walking cycle. Providing a suitable timing of toe-off, while providing a stable, level base—a preferable innovation addressed in this application—is lacking from existing feet prostheses and may be relevant for natural and comfortable ambulation.

The human gait is in reality a very complex process that at a basic level may be described as a series of repeating operations carried out by a single leg: 1) initial heel strike, 2) double support as both feet contact the ground, 3) stance phase as one leg supports the entire body weight, 4) pre-swing or heel-rise as the heel rises from the ground, 5) toe-off as the moment that the toes lose contact with the ground, and finally 6) swing phase, where the leg, acting as a pendulum, comes forward in preparation to repeat the process. In a two legged description of pre-swing, the heel of the contralateral leg strikes the ground at the exact moment that the ipsilateral heel rises. This is called double stance phase, and may be relevant to understanding the innovations presented in this application. Coordinated movement between the legs and the overall balance and trajectory of the body dynamic may be also relevant to successful ambulation.

Currently, there are two dominant paradigms of prosthetic foot design: post-like, conventional feet (CF) and leaf-spring-like, energy storing feet (ESF). Both of these designs change shape under loading, in an attempt to mimic the human foot. The classic CF foot, also known as the Solid Ankle Cushioned Heel (SACH), foot may provide a stable base for support, and is functionally unchanged since its conception in the 1960's. Introduced in the 1980's, carbon-fiber, leaf-spring ESF designs allow amputees to run by mimicking the ankle plantar flexors, returning energy to their stride. Para-lympic records rivaling their Olympic counterparts show that the ESF paradigm works very well for running, but studies have failed to show that these benefits extend to walking. 40% of transtibial amputees do not use prostheses and 78% of transfemoral amputees forego this intervention. Thus, over 120,000 amputees do not use prosthetic legs, preferring wheelchairs or crutches, never walking again. Studies of amputee psychosocial adjustment have linked positive emotional coping and higher levels of physical independence.

Depending on the type of foot used, CF or ESF, and the specific manufacturer, there have been subtle but significant differences in parameters such as stride length, symmetry of stride, and timing of the various phases of gait. For either foot type, stride length is shorter for strides where the prosthesis is the supporting limb, gait symmetry is markedly decreased, and the timing of the phases of gait may be disrupted. Most notably, there is a shortened stance phase on the prosthesis, a late toe off, and a longer swing phase on the affected side as well. Studies also describe an early incidence of low back and patellar-femoral osteoarthritis in unilateral amputees. The literature clearly shows that current prostheses fail to walk like an intact limb. In fact, clinical prostheticists have expressed the opinion that some "middle ground" between the unsophisticated CF feet and the highly athletic ESF feet is needed. Embodiments of the invention outlined here may be just that middle ground.

To lay the foundation for the rest of this submission, a few questions may be asked. Precisely how may an intact limb walk? And what is the role of the foot in this process? To address the first question, this application may present two different types of engineering control systems, and may provide illustrative examples. To address the second question, more studies may be presented, furthering the discussion, showing results of highly detailed, instrumented gait studies of the foot. Comparisons between the functional movements of the human foot, and the functional movements of current prostheses may follow. The improvements embodied in embodiments of the proposed device may address many of the shortcomings seen in the current technology.

With all of the myriad muscles and bones in human hips, legs, and feet, there is no "right" answer for how to propel one's self across a room or up a slope; however, there may be more optimal solutions, for example, ones that may be less abusive to the anatomy and/or ones with more optimal energetic efficiency. Early incidence of osteoarthritis, a degenerative joint change, is one indicator of a suboptimal movement strategy.

There may be many ways to walk, and data shows that people don't walk in exactly the same way with each stride. The hips may work harder on some strides than others; sometimes the lower leg may contribute varying amounts torque to the stride. Walking from one's hips may be described as a "top-down" control mechanism, where forces from the proximal leg may dictate the position and accelerations of the distal structures. This mechanism is very clearly illustrated in above knee (AK) amputees. Until recent, expensive innovation of computer controlled knees, AK amputees who wanted to walk faster than the return rate of their knee spring had to use a "hip snap," flinging their prosthesis out quickly with their hip flexors, and then quickly contracting their hip extensors to snap the prosthetic knee straight in time for heel-strike. Thus, the anatomic ranges of motion guided the position of the prosthetic anatomy, but the timing the movement was controlled by the hip, in a "top-down" fashion.

A "top-down" control mechanism may also be seen in studies of trans-tibial amputees. The iEMG data of one study showed a greater use of the biceps femoris (BF) as compared to the antagonistic vastus medialus (VM) in the amputated limb, as opposed to the normal limb. The mean ratios of BFNM activity during the first half of stance phase was 3.8 in the amputated limb and 2.0 in the sound leg, with a P value of less than 0.042. Furthering elaboration on the "top-down" nature of this control system, an exceptionally statistically rigorous study from 2002 revealed some interesting trends in the flexor/extensor ratios for the knees of unilateral, trans-tibial amputees, as compared to normal volunteers. Though the amputees were much weaker than the normal control group, this study showed that there was no significant difference between the knee flexor/extensor ratios for peak bending moment, total work, or maximum power comparing either leg of the amputees and either leg of the non-amputees. Of course, the BF and VM may be also knee flexors and extensors, but not during the relevant time-span cited by the first study, early stance phase. Considering these studies together, one may conclude that trans-tibial amputees use the hip of the amputated leg more than the hip of their sound leg, and that they use their knee flexors and extensors normally. Clearly, the control mechanism being employed in a trans-tibially amputated limb is "top-down."

The overuse of a particular muscle must result in overuse of the surrounding and supporting muscles. For example over loading a hip muscle causes the hip stabilizers to be over-recruited. If multifidus and transversus abdominus, the deepest pelvic stabilizers, may be overwhelmed, the larger quadratus lomborum (OL) and erector spinae (ES) muscles that may be normally used for motion may be recruited to help it. When the QL and ES are used as stabilizers, the agonists may also be recruited as stabilizers, just as transverses abdominus is recruited along with multifidus. When the QL and ES become a routine part of the stabilizing muscle pattern, they become tonic and rigid. Thus, putting a great deal of compression on the spine. This is a well-known pattern of muscle use and, if allowed to progress unchecked, may eventually result in degenerative joint changes in the lower spine.

Walking from the foot, as opposed to the hip, may be modeled as a "bottom-up" control scheme, where the distal anatomy directs the position of the proximal anatomy. The coordination of the metatarsophalangeal joint (MTP) of the great toe and the subtalar joint may create a dynamic in gait where the proximal foot and tibia subtly change angular position. This angular change may be the start of building momentum for toe off. In context of the gait cycle, starting from single stance phase, as the tibial shaft moves past perpendicular and over the foot, the subtalar joint may be eccentrically loaded. This may be seen as a "flatter" transverse arch. This subtle motion may progress with the tibial shaft advancement, with a maximum angular change of 10 degrees. In double stance phase, much of this weight may be off-loaded to the other leg, but the transverse arch may not yet spring back into shape. In fact, this new conformation may be maintained until just after heel rise. When the heel leaves the ground, passing the remaining force loading to the ball of the great toe, the MTP of the great toe may be forced into extension. This motion may pull on the plantar aponeurosis, which in turn may pull on the calmayeus and the Achilles tendon. This action may loft the transverse arch back to its stance phase conformation, subtly altering the position of the ankle and the tibia, and thus may change position of the knee and hip.

The relevant anatomy for this coordination of the first MTP and subtalar joints is well documented. The plantar aponeurosis spans both joints, as may the tendon of the flexor hallucis longus. Different research references attribute this coordination to each of these sources. The action of arching the subtalar joint by forcibly extending the first MTP has been described as the Windlass mechanism, and this passive, non-muscular change may be a function of timing and anatomic length. This timing may be influenced by the peronii, the tibialis anterior, and the intrinsic foot muscles. Of course, a passive prosthesis may not duplicate the action of these muscles, but it may mimic the action of the plantar aponeurosis. Due to the quasi-psuedoviscoelastic nature of the plantar aponeurosis and the surrounding musculature, this quick lofting of the plantar arch may be an energy storage mechanism. The energy may then be released, a moment later, on toe off. As seen in the temporal gait asymmetry of amputees, most notably in late stance and swing phases, studies have shown conclusively that this action is not accomplished in either CF or ESF designs.

These two distinct "ways of walking" represent extremes, and, as human nature dictates, we all walk with a varying degree of each mechanism. Amputees must rely exclusively on the strategy of top-down control, resulting in an overcompensation of the remaining anatomy which in turn may cause early degenerative changes. What is needed is a prosthesis that accurately imitates the relevant biomechanics of the natural foot, allowing for the contributions of the more efficient "bottom-up" gait style.

There is a definite coordination between the joints of the foot. The angular relationship shown between the forefoot and hallux may be the angular position of the first MTP. The angular motion between the forefoot and hindfoot may reflect the motion of the subtalar joint. A few studies have explored the detailed biomechanics of the foot using this powerful analytical technique, but they did not combine the detailed foot analysis with the protocol for the rest of the body. Thus, no quantified joint powers were generated. Experts may also be aware of the subtle, but highly significant errors in instrumented gait analysis of ESF prosthesis gait. Failure to accurately model the center of curvature of the leaf spring foot, for the purpose of reverse engineering the joint torques, may be the documented source of this error. The standard seven segment lower body model, used to reverse engineer joint torques, may use a rigid single segment foot. This simplified model may leave out both the first MTP and the subtalar joints, masking the relevant contribution of the Windlass mechanism, a subtle "bottom-up" contributor of gait mechanics. Theoretically, a nine segment lower body model, as seen in computer simulations, may show sensitivity to changes in spring stiffness of the MTP joint at push off, but still may exclude the subtalar joint or any coordination of the two.

The movement of the subtalar joint and first MTP during stance phase and toe-off, as described above, may correlate to a relatively new area of prosthetics research. Roll-over shape may be defined as the geometry a foot/ankle complex takes during the single limb stance phase of walking. As the center of weight may pass over the long axis of the prosthetic foot, it may bend according to its stiffness. The shape described by this bending may be the rollover-shape, and it may be defined in general terms as a rigid rocker model of the foot/ankle complex. A three dimensional rollover shape may be called a rollover surface, and a two dimensional shape may be called a rollover profile.

Studies of various prosthetic feet with the rollover profile methodology have shown that the "effective foot length" during walking is surprisingly short in many cases. For example, a size 28 cm SACH foot may display a functional length of less than 20 cm. The length of the rollover profile is significant for many gait parameters, and recent studies show that it may be relevant to how much oxygen is consumed during gait.

Considering the rollover profile length, along with the recent research into oxygen consumption dynamics, points toward a discrepancy that may be more significant than previously thought. In fact, the energy used in walking may be proportional to the fourth power of the step length. Since the stride length may be equal to the functional foot length plus the distance covered by swing phase, feet with shorter rollover profiles may deliver shorter stride lengths. The average step length is about 0.75 meters, and the difference in rollover profile between a SACH foot and a flex-foot is about 6 centimeters. Considering the relationship described above, one would anticipate a large energy savings by using the longer flex-foot, because the step length is almost 10% greater for the ESF versus over the CF. Surprisingly, this energy savings is not seen in any ESF models with longer rollover profiles. In fact, research shows a small energy savings, on the order of 3%, and some of the research subjects in that study found that some ESF feet were more tiring to use than some CF feet. This correlates well with the experience of clinical prosthetists, who describe that their patients often work against their ESF feet, because their return of power is not biomechanically accurate. Indeed, studies of prostheses show that a very small component of this energy return is in the antero-posterior direction, unlike the natural human limb.

SUMMARY

There is a need for improved artificial foot devices. In particular, there is a need for artificial foot devices that more accurately simulate the motion and or function of the human foot during walking.

In one embodiment, an artificial foot device may be provided. The artificial foot device may include: a core; a talus body operatively coupled with the core by a first joint that provides for constrained relative movement between the talus body and the core; and a toe operatively coupled with the core by a second joint that provides for constrained relative movement between the core and the toe.

In some embodiments, the core may include a core assembly including a core body, an Achilles sheave coupled with the core body and a toe bracket coupled with the core body. In such embodiments, the toe bracket may be operatively coupled with the toe.

In some embodiments, the first joint may include at least a first tension rope coupling the talus body and the core. In some embodiments, the second joint may include at least a first tension rope coupling the core and the toe.

In some embodiments, the first joint may include a second tension rope coupling the talus body and the core. The first tension rope may constrain relative movement of the talus body and the core in at least a first direction, and the second tension rope may constrain relative movement of the talus body and the core in at least a second direction different from the first direction.

In some embodiments, the second joint may include a second tension rope coupling the core and the toe. The first tension rope may constrain relative movement of the core and the toe in at least a first direction, and the second tension rope may constrain relative movement of the core and the toe in at least a second direction different from the first direction.

In some embodiments, the first joint may permit limited relative rotation of the talus body and the core about a first lateral axis, with the talus body, the core and the toe defining a longitudinal direction of the artificial foot. Alternatively or additionally, the first joint may permit limited relative rotation of the talus body and the core about a first longitudinal axis. Alternatively or additionally, the first joint may permit limited relative rotation of the talus body and the core about a substantially vertical axis.

In some embodiments, the second joint may permit limited relative rotation of the talus body and the core about a first lateral axis. Alternatively or additionally, the second joint may permit limited relative rotation of the talus body and the core about a first longitudinal axis. Alternatively or additionally, the second joint may permit limited relative rotation of the talus body and the core about a substantially vertical axis. Alternatively or additionally, the second joint may permit limited relative lateral movement between the core and the toe.

In some embodiments, the first joint may include means for constraining relative movement between the talus body and the core other than about a lateral axis. In such embodiments, the means for constraining relative movement between the talus body and the core other than about a lateral axis may be configured to constrain relative movement between the talus body and the core about a longitudinal axis and/or about a substantially vertical axis.

In some embodiments, the second joint may include means for constraining relative movement between the core and the toe other than about a lateral axis. In such embodiments, the means for constraining relative movement between the core and the toe other than about a lateral axis may be configured to constrain relative movement between the core and the toe about a longitudinal axis and/or about a substantially vertical axis.

In some embodiments, the constrained relative movement between the talus body and the core may substantially correspond to a coordinated movement of a first natural joint and a second natural joint during ambulation of a natural human foot. In such embodiments, the constrained relative movement between the core and the toe may substantially correspond to a coordinated movement of a third natural joint, different from the first and second natural joints, during ambulation of a natural human foot.

In some embodiments, the artificial foot may include a coordination member operatively coupled with the talus body and the toe. In such embodiments, the coordination member may be configured to store and release energy during a walking movement of the artificial foot.

In some embodiments, the artificial foot may include at least one member operatively coupled with the core and the toe. In such embodiments, the at least one member may be configured to store and release energy during a walking movement of the artificial foot.

In some embodiments, a method of providing motion in an artificial foot device may be provided. The method may include coordinated movements of three or more structural members operatively coupled by two or more joints. The coordinated movements may be constrained by the two or more joints and/or interactions between the three or more structural members.

In some embodiments, a method of providing motion in an artificial foot device may include constrained relative movement between a first structural member and a second structural member. Such constrained movement may substantially correspond to a coordinated movement of a first natural joint and a second natural joint during ambulation of a natural human foot.

In such embodiments, the method may include constrained relative movement between the second structural member and a third structural member. Such constrained movement may substantially correspond to a coordinated movement of a third natural joint, different from the first and second natural joints, during ambulation of a natural human foot.

BRIEF DESCRIPTION OF THE DRAWINGS

These and other features, aspects and advantages will be more fully understood when considered with respect to the following detailed description, appended claims and accompanying drawings, wherein:

FIGS. 23-28 illustrate an embodiment of the Achilles sheave of the core assembly illustrated in FIGS. 11-16.

FIGS. 29-33 illustrate an embodiment of the mid-foot bearing of the core assembly illustrated in FIGS. 11-16.

FIGS. 34-38 illustrate an embodiment of the toe bracket of the core assembly illustrated in FIGS. 11-16.

FIGS. 40-45 illustrate an embodiment of the toe of the artificial foot illustrated in FIGS. 1-4.

DETAILED DESCRIPTION

Figure 1:
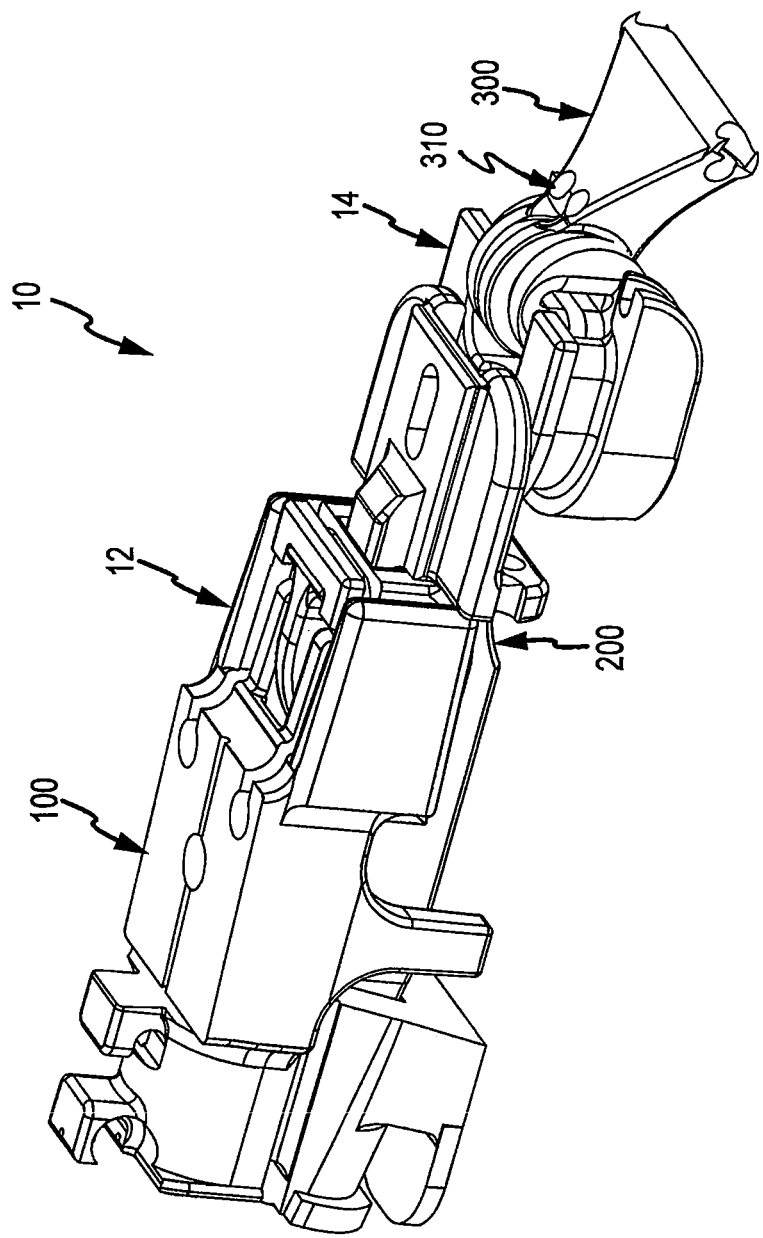
FIGS. 1-4 illustrate an artificial foot including a talus body, a core assembly and a toe according to an embodiment of the invention.

Various details are described below, with reference to illustrative embodiments. It will be apparent that the invention may be embodied in a wide variety of forms, some of which may be quite different from those of the disclosed embodiments. Consequently, the specific structural and/or functional details disclosed herein are merely representative and do not limit the scope of the invention.

For example, based on the teachings herein it should be understood that the various structural and/or functional details disclosed herein may be incorporated in an embodiment independently of any other structural and/or functional details. Thus, an apparatus may be implemented and/or a method practiced using any number of the structural and/or functional details set forth in the disclosed embodiments. Also, an apparatus may be implemented and/or a method practiced using other structural and/or functional details in addition to or other than the structural and/or functional details set forth in the disclosed embodiments.

Embodiments of the device proposed in this application may be based on the tensegrity design idea. Tensile-integrity, shortened to "tensegrity," may refer to a special type of structure comprising continuous tensile members (e.g., cables) acting upon discontinuous compressive members (e.g., spars). Tensegrity structures may rely upon the tensile strength and flexibility properties of wire rope to bear physical loads placed upon them. Major innovations in steel wire rope technology, driven by increasing performance demands in the automotive and aerospace sectors, now permit the construction of light weight joints that may be stronger in many cases than traditional engineered "beam and bearing" structures.

As used herein, "tensegrity" may refer to the characteristic of having two or more discontinuous members dispersed in a network of one or more continuous tension members.

As used herein, "tensegrity joint" may refer to a joint having a tensegrity structure. In a tensegrity joint, the two or more discontinuous members may be incompletely constrained by the network of the one or more continuous tension members in which they may be dispersed, whereby the members may be able to move relative to each other. The movement may be at one or more centers of motion, and optionally around a primary axis at each center. Optionally, the primary axis may be virtual and not coaxial with an actual tension member. As described herein, in addition to the constrained or limited range of relative motion of the discontinuous members of the joint provided by the tension member(s), contact between the discontinuous members may also constrain or limit the relative motion.

As referred herein, dorsiflexion may be defined as motion in the direction of the top of the foot (e.g., dorsal surface), and plantarflexion may be defined as motion in the direction of the bottom of the foot (e.g., plantar surface).

In a tensegrity joint, the discontinuous members may be rigid, and the number, length, diameter, geometric organization, and flexibility characteristics of the tension members may determine the range of motion of the discontinuous members. Tension members may constrain and/or stabilize the discontinuous members.

Further, a tensegrity approach may be employed to couple movements of multiple joints. For example, the movement or motion of a first joint may be coupled to movement/motion of a second joint via one or more tension members, such as a coupling cable. The coupling cable(s) may connect two discontinuous members that may not be connected by a single joint, but indirectly connected by two or more joints.

Each joint in the animal body may have its own specific geometry. Joint(s) in embodiments of the invention may be designed to have similar characteristics of natural joints. Alternatively, super joints may be designed for prosthetics, orthotics, and robotics that do not interfere with the functioning of the remaining joints of the body or robot.

The materials of the discontinuous and tension members may be selected to maintain structural integrity considering the use of the device and the user of the device. Devices that must withstand greater forces may be made from stronger materials.

As used herein, "rope" may refer to an element capable of functioning as a tension member in a tensegrity joint, such as cables having a diameter less than about ¼ inch, for example. An effective rope element may comprise two or more thinner ropes, including a thin rope making multiple passes and having a larger effective diameter than the thin rope alone. Generally, these ropes may not be elastic.

Orthotics may augment body parts. Prosthetics may replace body parts. Robotics may function similarly to body parts, but may not require direct connection to a body in order to be functional.

Limit ropes and stabilization ropes may be tension members in tensegrity joints that limit the ranges of motion of the joint. Optionally, the tensegrity joint may have a primary axis of motion. A primary axis of motion may be the least constrained axis of all the other axes of motion of the joint. Optionally, one tension member may be coaxial with the primary axis of motion of the joint. Alternatively, the primary axis of motion may not be coaxial with a tension member, and the primary axis may then be said to be virtual.

Figure 2:
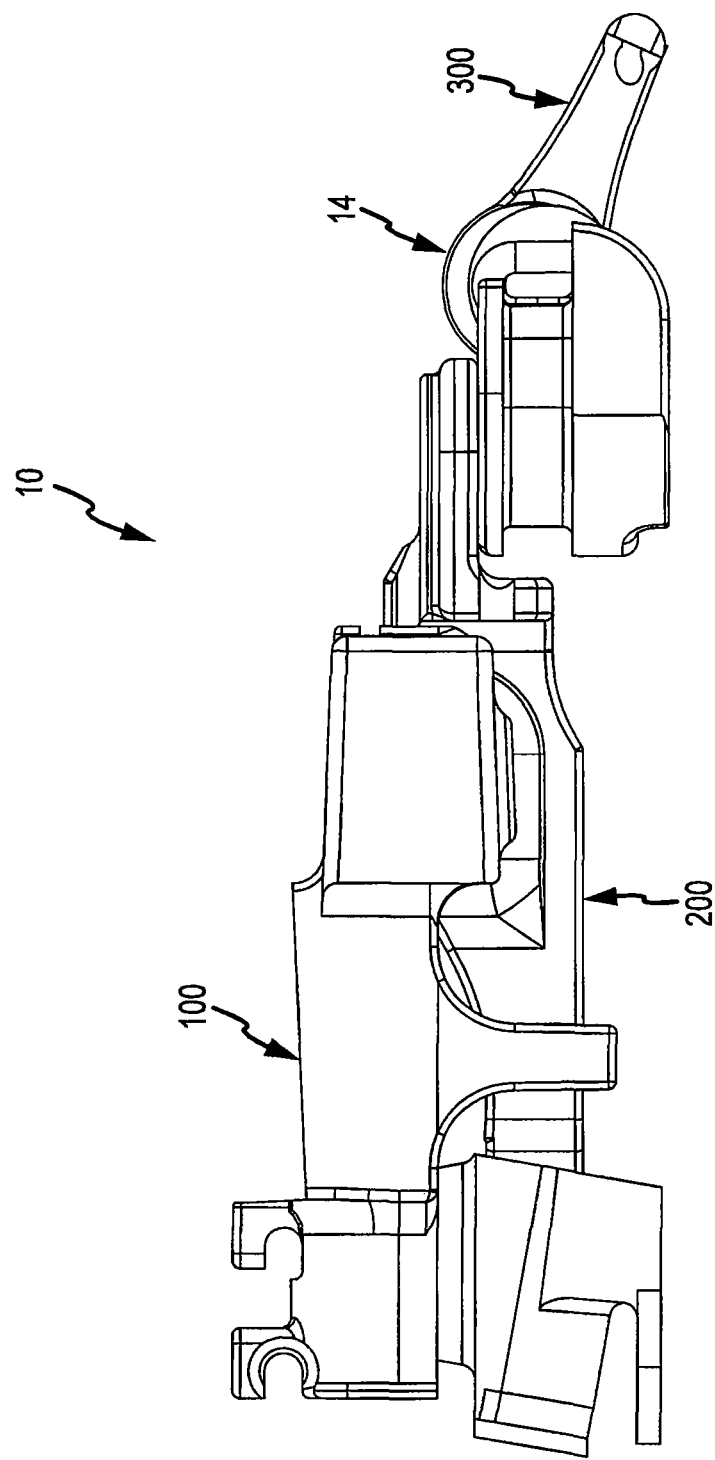
Figure 3:
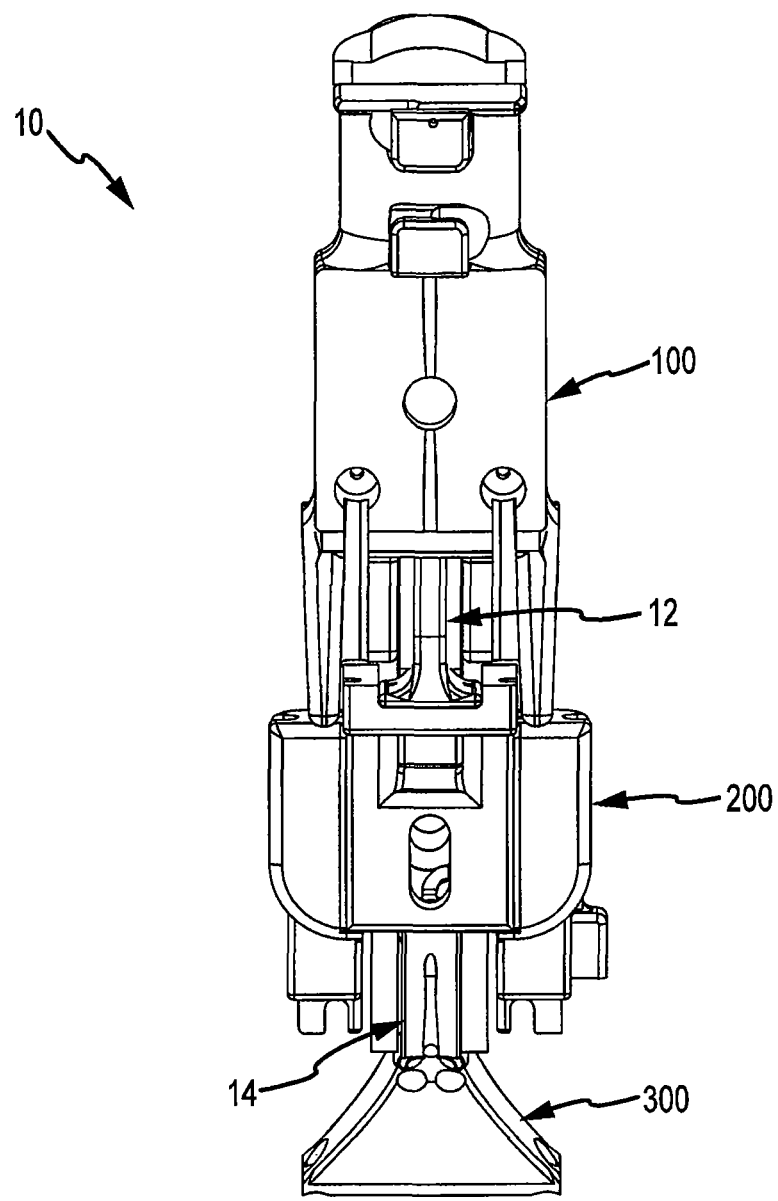
Figure 4:
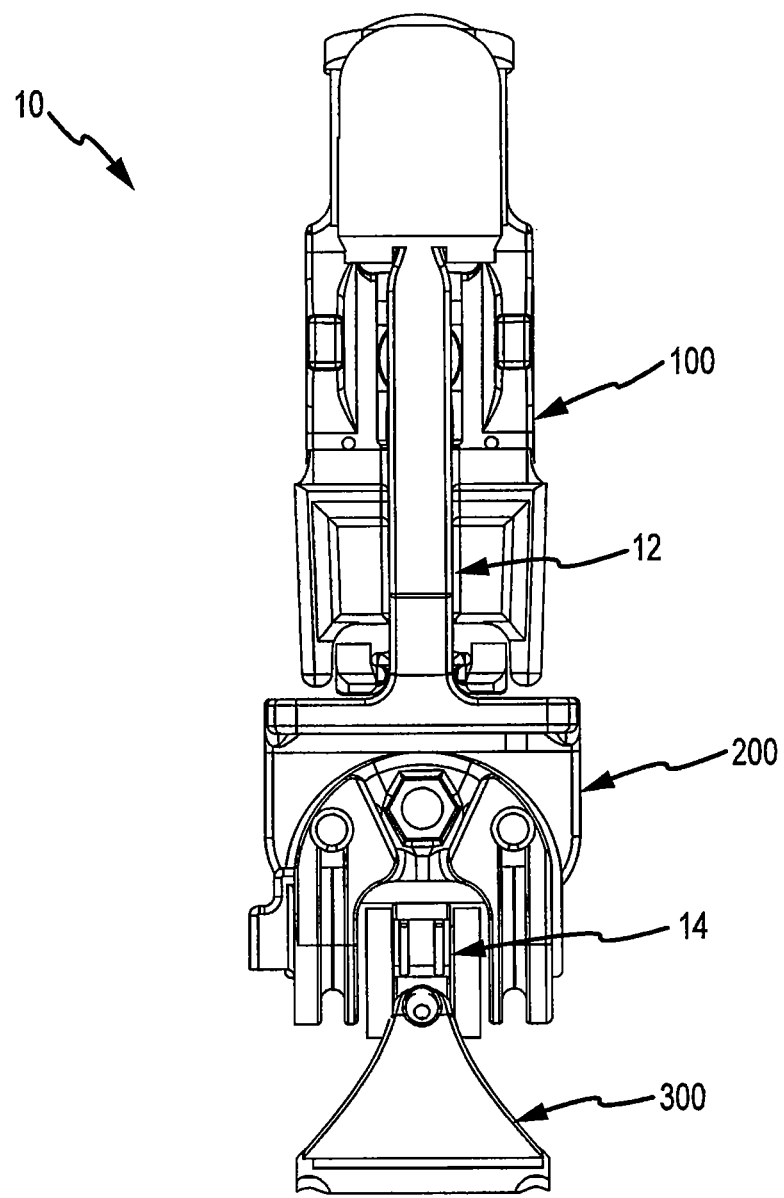

FIGS. 1-4 illustrate an artificial foot 10 including a talus body 100, a core assembly 200 and a toe 300 according to an embodiment of the invention. FIG. 1 depicts a perspective view of the artificial foot 10. FIG. 2 depicts a right side view of the artificial foot 10. FIG. 3 depicts a top view of the artificial foot 10. FIG. 4 depicts a bottom view of the artificial foot 10.

The talus body 100 may be operatively coupled with the core assembly 200 via a first joint 12. The core assembly 200 may be operatively coupled with the toe 300 via a second joint 14. As described herein, it should be understood that the first and second joints 12, 14 include one or more tension members, such as ropes, which are not shown in these FIGS. for simplicity. As discussed above, the tension member(s) may constrain movement of the talus body 100, the core assembly 200 and the toe 300. An example of the artificial foot 10 including tension members is illustrated in FIGS. 50-56, discussed below.

Although not shown in FIGS. 1-4, it should be understood that a pylon may be coupled to the talus body 100, for example, when the artificial foot 10 is configured to serve as a prosthesis. As discussed herein, the artificial foot 10 may provide a more natural walking motion for the user because of the joints 12, 14 operatively coupling the talus body 100, the core assembly 200 and the toe 300. Details of specific embodiments of the talus body 100, the core assembly 200 and the toe 300 are discussed below.

Figure 5:
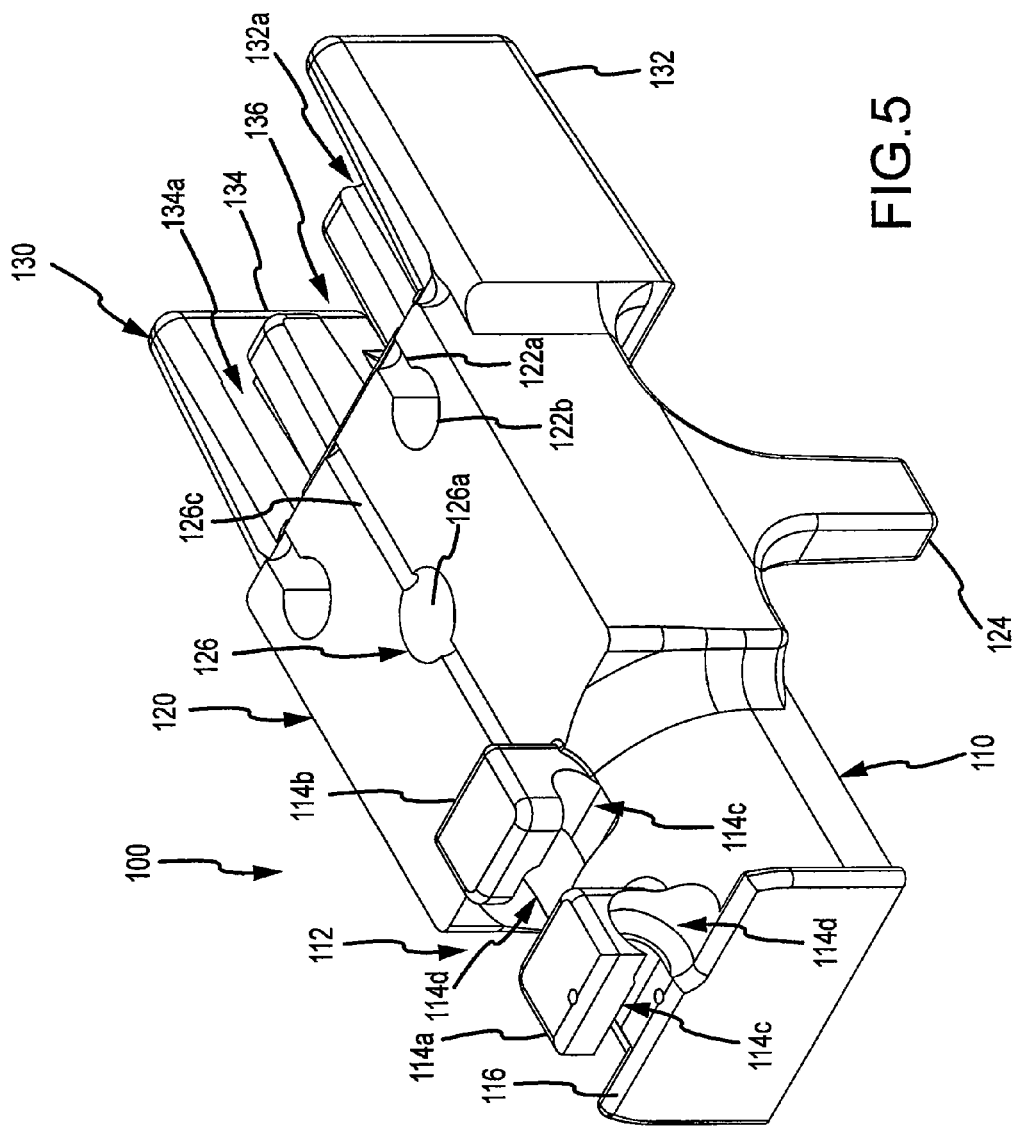
FIGS. 5-10 illustrate an embodiment of the talus body of the artificial foot illustrated in FIGS. 1-4.
Figure 6:
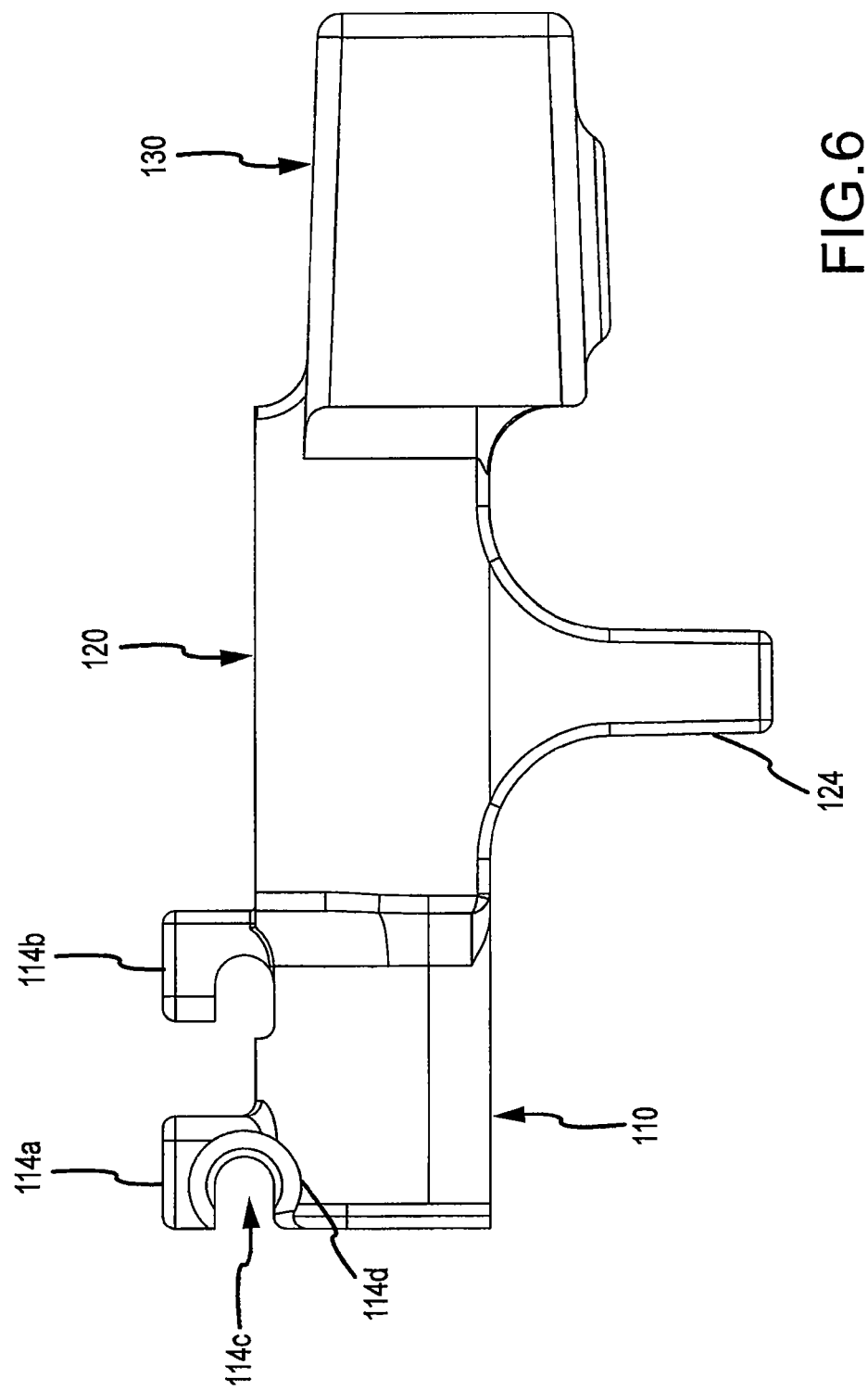
Figure 7:
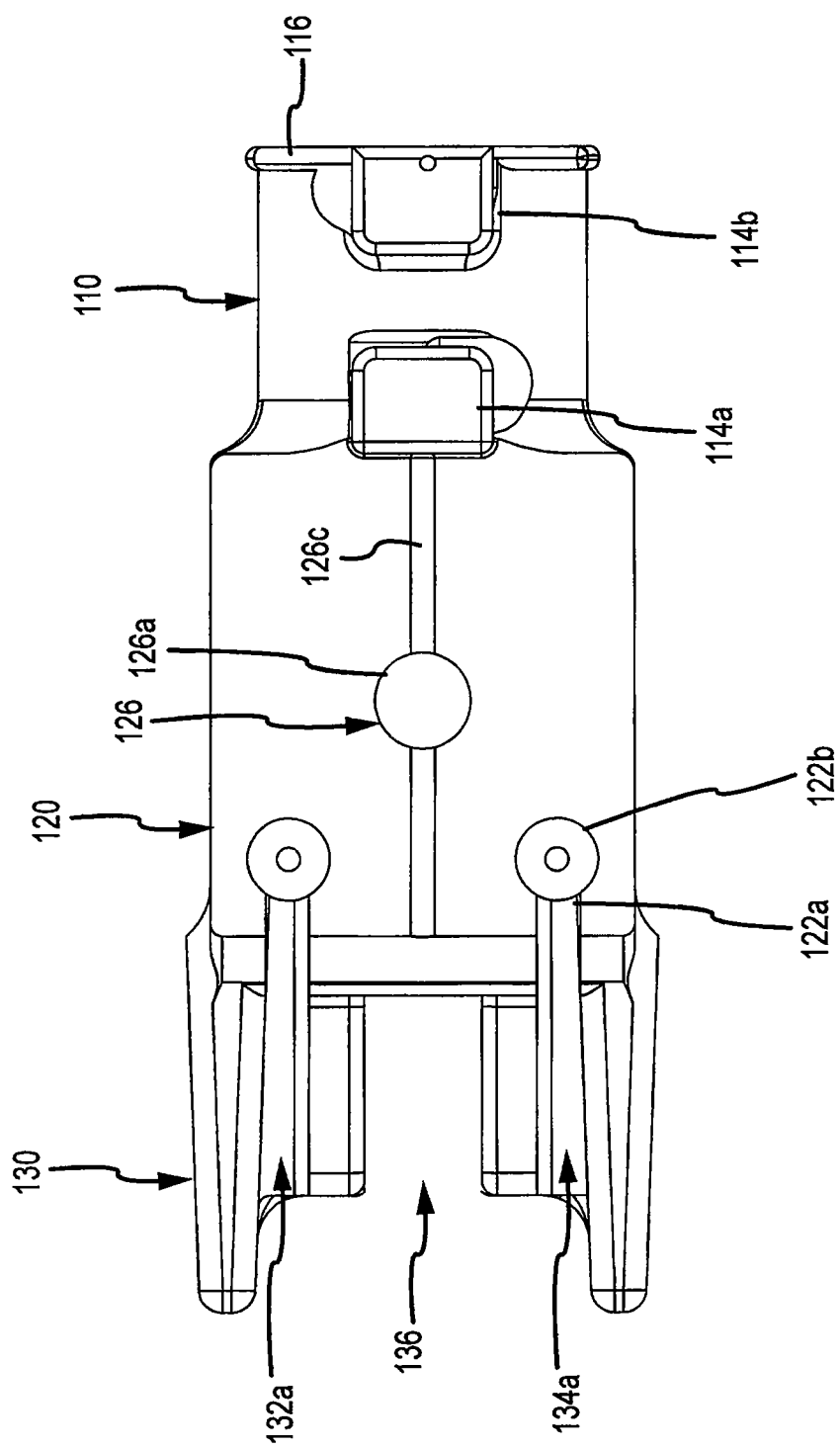
Figure 8:
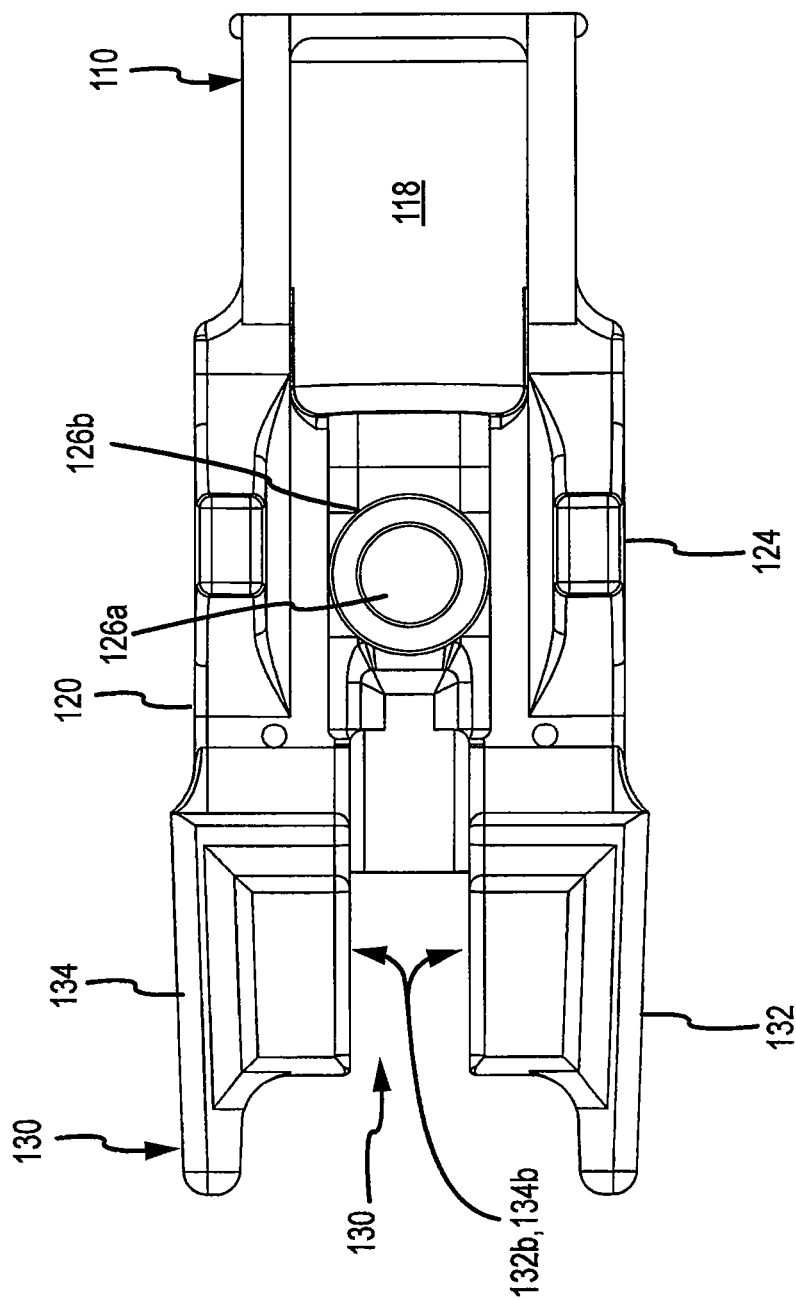
Figure 9:
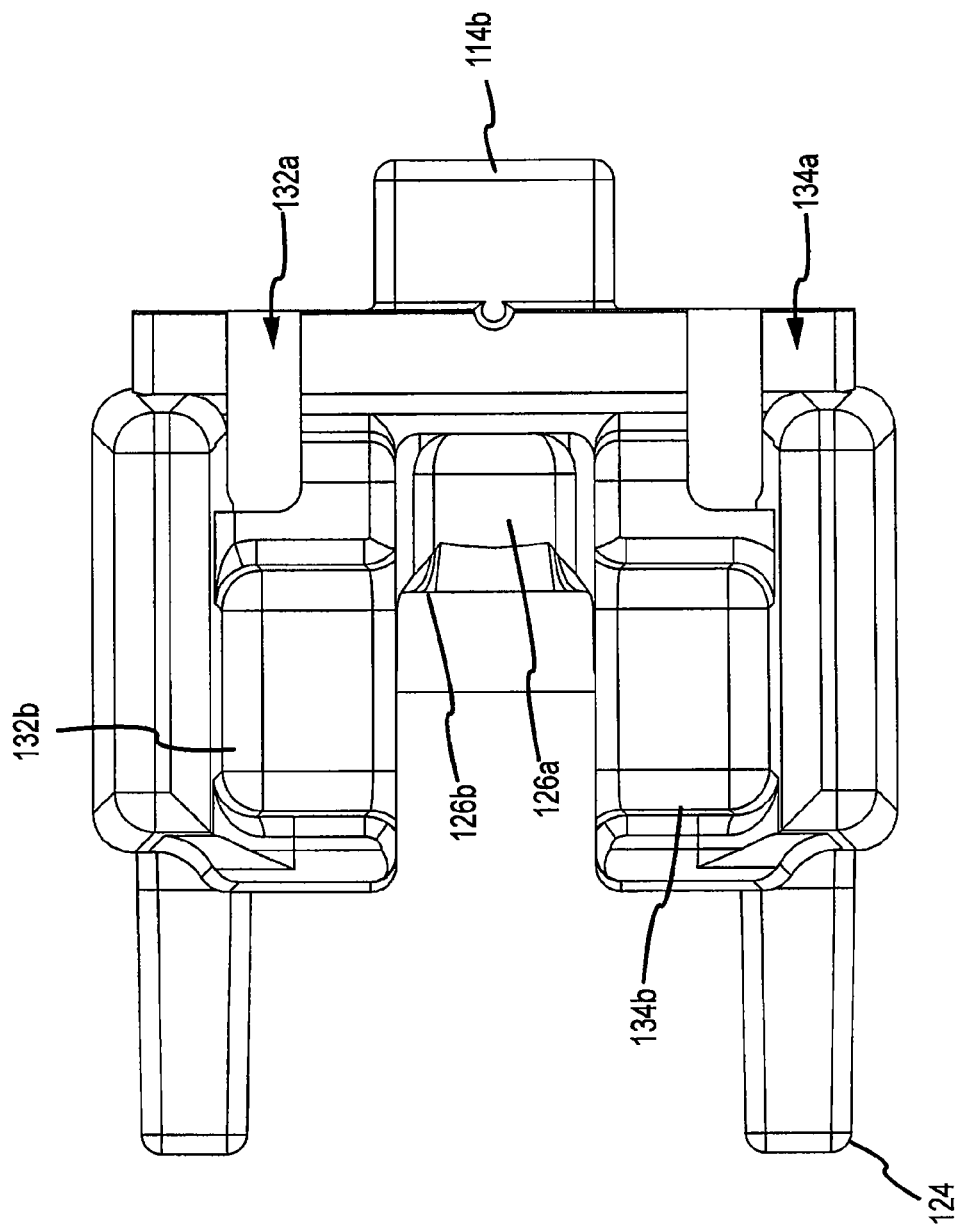
Figure 10:
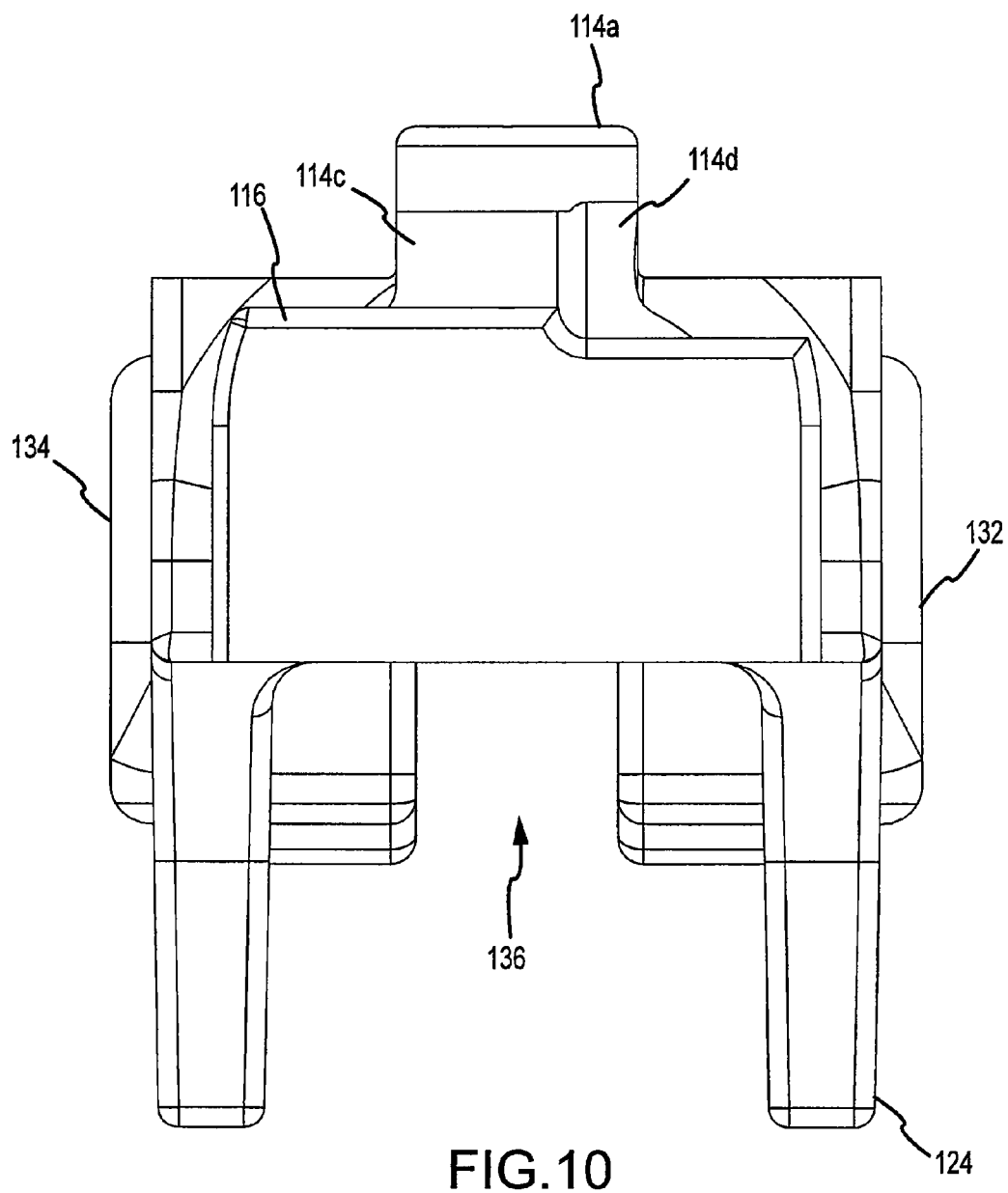

FIGS. 5-10 illustrate an embodiment of the talus body 100 of the artificial foot 10 illustrated in FIGS. 1-4. FIG. 5 depicts a perspective view of the talus body 100. FIG. 6 depicts a right side view of the talus body 100. FIG. 7 depicts a top view of the talus body 100. FIG. 8 depicts a bottom view of the talus body 100. FIG. 9 depicts a front view of the talus body 100. FIG. 10 depicts a rear view of the talus body 100.

The talus body 100 may be described as including a rear section 110, a mid-section 120 and a front section 130, with the toe 200 defining a front of the artificial foot 10 for the sake of clarity.

The rear section 110 may include a first rope retaining means 112 for retaining an associate tension rope (not shown). The first rope retaining means 112 may include first and second protrusions 114a and 114b. The first and second protrusions 114a and 114b may include grooves 114c, which may open to the rear as shown. The first and second protrusions 114a and 114b may also include recesses 114d opening into the respective grooves 114c at opposite sides. The recesses 114d may be semi-spherical, for example, to receive and retain a respective spherical or semi-spherical end of an associated rope.

It should be understood that the particular configuration of the rope retaining means 112 may vary based on the particular implementation. For example, the one or both of the grooves 114c may open to the front. Thus, the grooves 114c may open in a same or an opposite direction, as appropriate or desired.

Further, the shape of the recesses 114d may vary, for example, based on the shape of the ends of the associated rope. Moreover, the first and second protrusions 114a and 114b may include through holes with or without recesses, and any desired number of protrusions may be employed.

The rear section 110 may also include a rear flange 116, which may also serve to retain the associated rope relative to the talus body 100. It should be understood that a protrusion may be suitably disposed to provide the function of the rear flange 116, such as a protrusion with a front-opening groove disposed at a rear edge of the rear section 110. In general, any suitable configuration of a rope retaining means may be implemented at the rear section 110.

The rear section 110 of the talus body 100 may also include a recess 118 in an underside thereof. The recess 118 may extend into an underside of the mid-section 120 as shown in FIG. 8, or may be limited to the rear section 110, as appropriate or desired. Further, the recess 118 may be at least partially filled with a suitable material for cushioning as the Achilles sheave 220 moves toward the talus body 130. Any suitable elastic material mat be used, such as urethane, and the recess 118 may be filled or otherwise contain a suitable amount of such material. For example, the material need not extend to the edges of the recess 118. Various degrees of cushioning may be provided by the cushioning material, for example, by varying the elasticity of the urethane.

The mid-section 120 of the talus body 100 may include a second rope retaining means 122. The second rope retaining means 122 shown includes a first and second grooves 122a and first and second recesses 122b that open into the respective grooves 122a. The recesses 122b may be cylindrical as shown, or may be any suitable configuration to cooperate with a corresponding end of the associated rope. It should be also understood that the second rope retaining means 122 may be implemented in any suitable configuration other than the groove and recess combination shown. For example, holes in a portion of the talus body 100 may be employed that allow an end of the associated rope to be extended therethrough and then secured by a nut, a clamp, a ball or the like that cannot pass through the hole.

The mid-section 120 of the talus body 100 may include right and left downward extensions 124. The extensions 124 may include respective holes, grooves and/or recesses (not shown) to provide rope retaining means for an associated rope, such as discussed further below.

The mid-section 120 of the talus body 100 may include a coupling or engagement means 126 configured to couple/engage with a pylon, for example, as in the case of the artificial foot being implemented as a prosthesis. The coupling/engagement means 126 may include a bore 126a through the talus body 100, as well as a recess 126b in the bottom of the talus body 100 that opens into the bore 126a. In such case, the pylon may be coupled to the talus body 100 by a bolt (not shown) extending through the bore 126a and secured by a nut (not shown) fitted into the recess 126b, which may be configured to limit or prevent relative motion of the nut. Further, the coupling/engagement means may include an anti-rotation groove 126c, which may be disposed longitudinally as shown or otherwise. The groove 126c may be configured to cooperate with a corresponding protrusion on the pylon. Of course, the location of the groove and the protrusion may be reversed.

The front section 130 of the talus body 100 may include a right flange 132 and a left flange 134 that extend forwardly from the mid-section 120. The right and left flanges 132,134 may include respective grooves 132a, 134a configured to receive an associated rope secured by the second rope retaining means 122. A central channel 136 may be defined between the right and left flanges 132, 134. The central channel 136 may be configured to receive a portion of the core assembly 200, as discussed further below. Further, bearing recesses 132b and 134b may be defined in an inner wall of the respective right and left flanges 132, 134 for receiving pivot bearings, as discussed below with respect to FIG. 39. In particular, the bearing recesses 132b, 134b may be open in the direction of view illustrated in FIG. 9. Further, the bearing recesses 132b, 134b may allow for a desired degree of movement of the bearings within the bearing recesses 132b, 134b.

Figure 11:
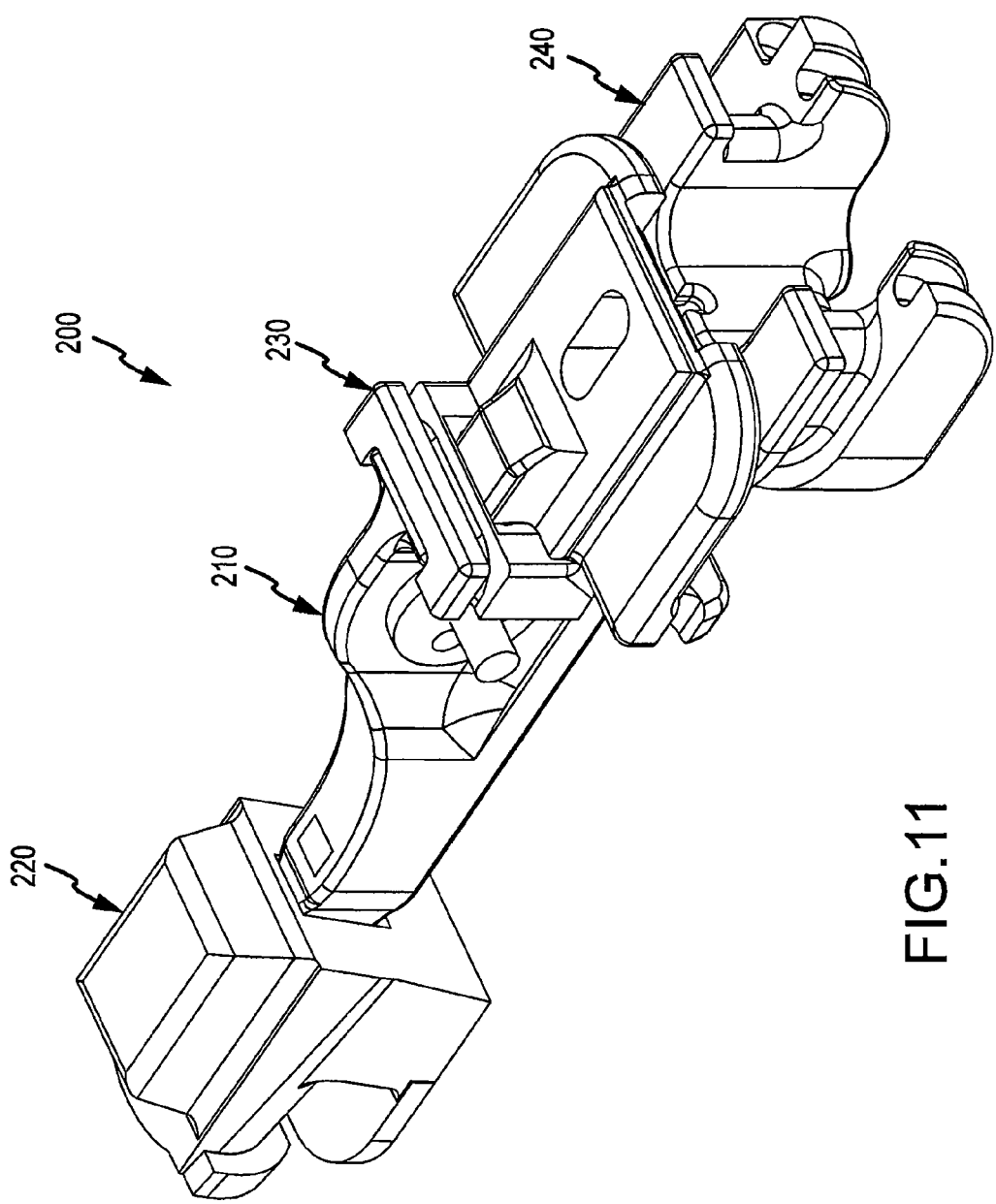
FIGS. 11-16 illustrate an embodiment of the core assembly of the artificial foot illustrated in FIGS. 1-4.
Figure 12:
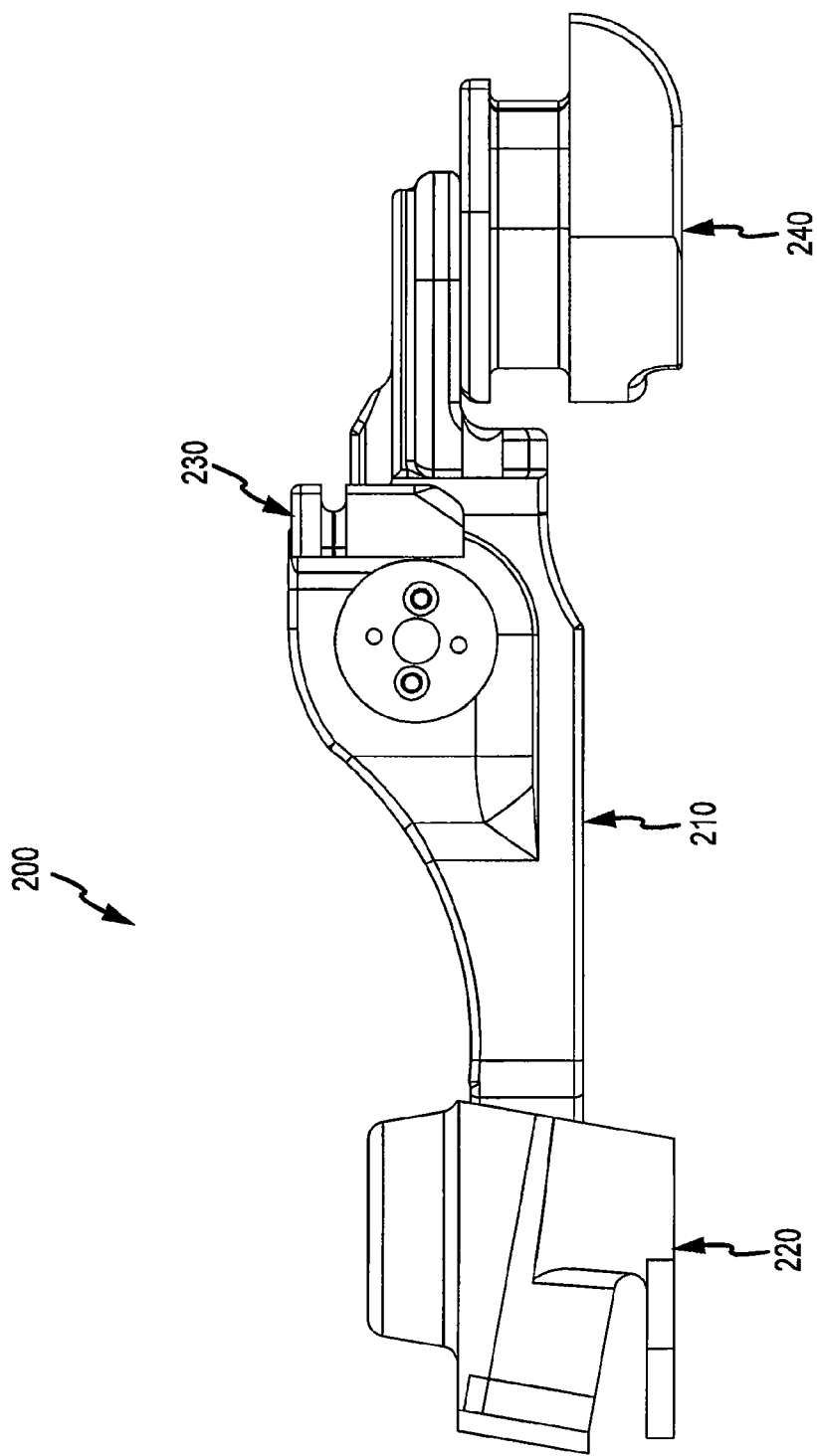
Figure 13:
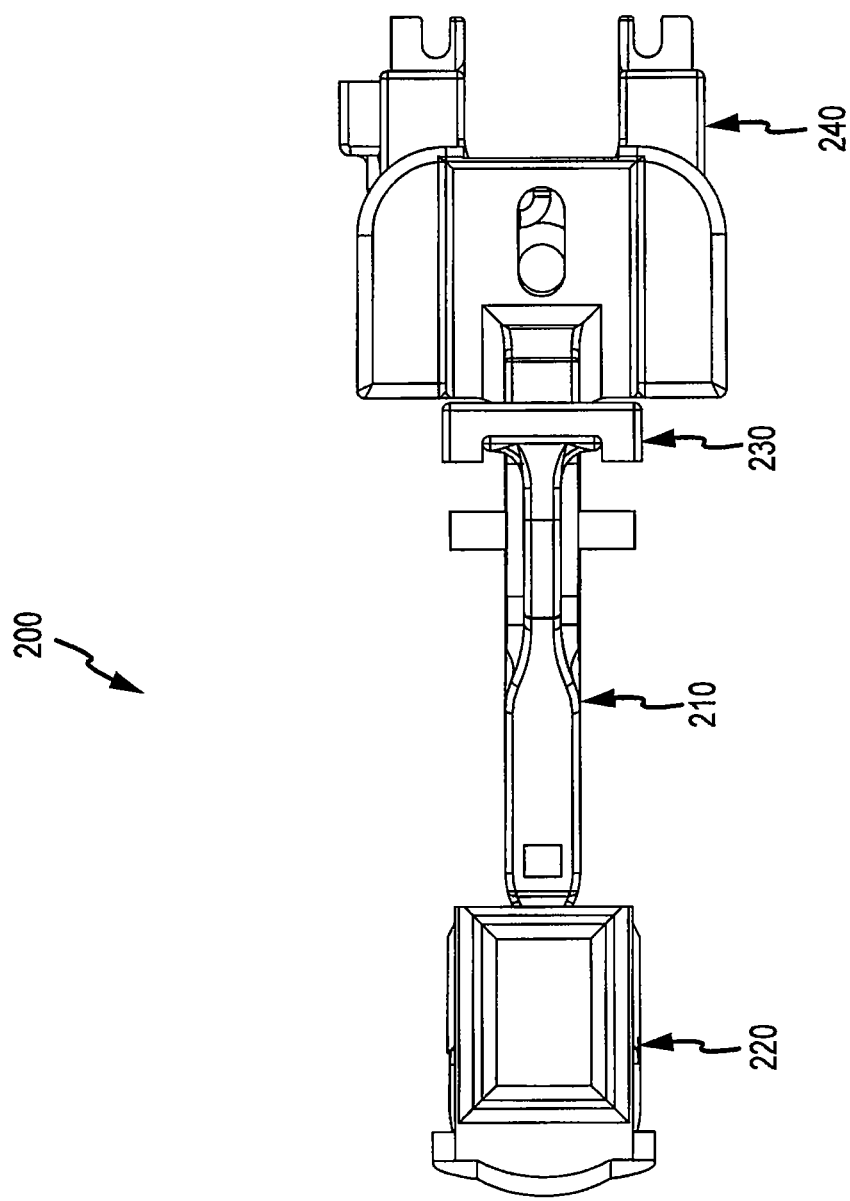
Figure 14:
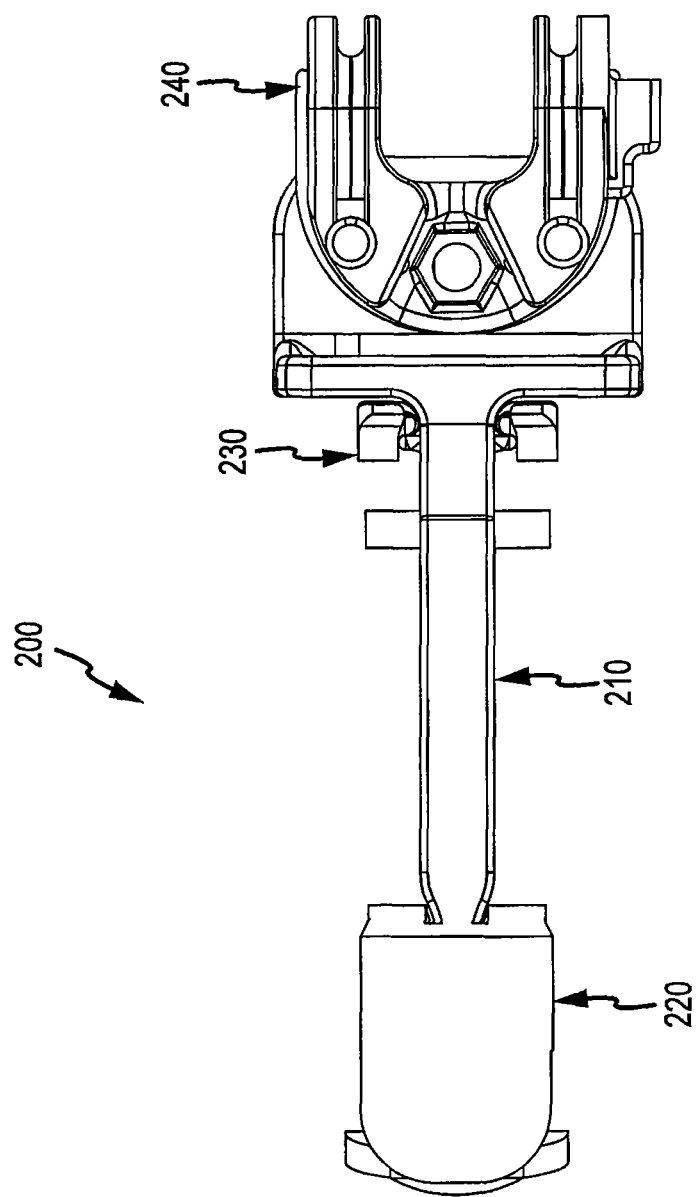
Figure 15:
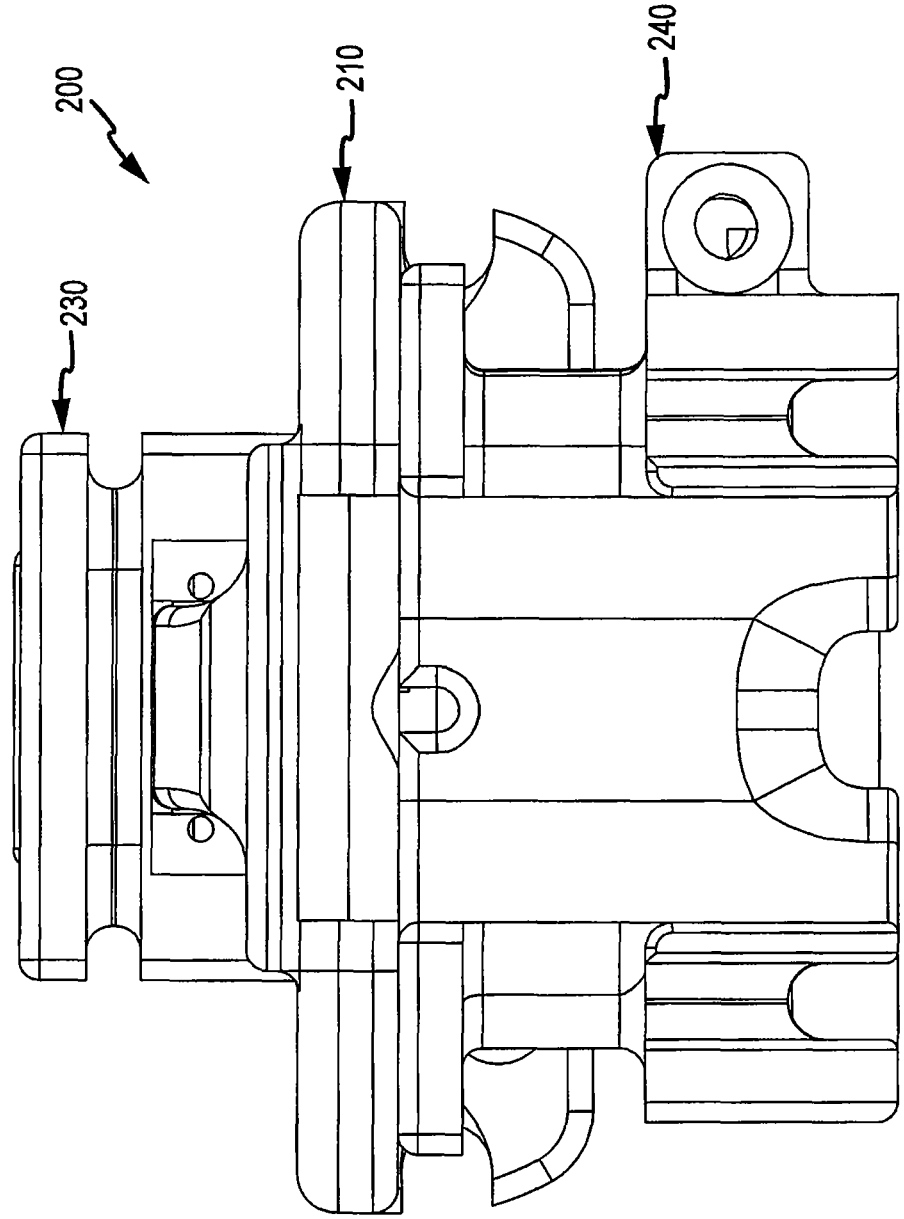
Figure 16:
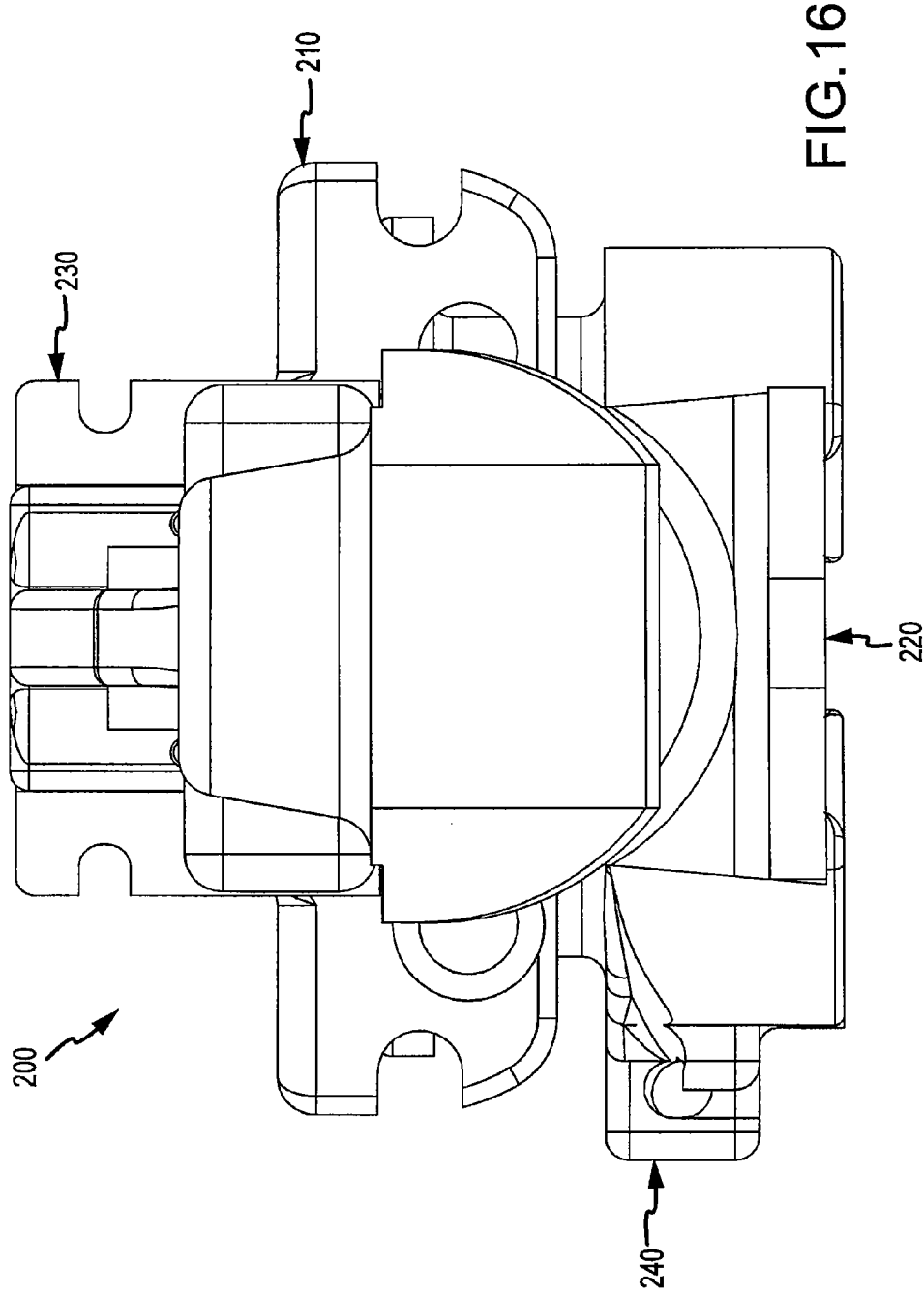

FIGS. 11-16 illustrate an embodiment of the core assembly 200 of the artificial foot 10 illustrated in FIGS. 1-4. FIG. 11 depicts a perspective view of the core assembly 200. FIG. 12 depicts a right side view of the core assembly 200. FIG. 13 depicts a top view of the core assembly 200. FIG. 14 depicts a bottom view of the core assembly 200. FIG. 15 depicts a front view of the core assembly 200. FIG. 16 depicts a rear view of the core assembly 200.

The core assembly 200 may include a core body 210, an Achilles sheave 220, a mid-foot bearing 230 and a toe bracket 240. These components may be positioned as shown, and coupled to each other via ropes and/or other coupling/engagement means, as discussed further below.

Figure 17:
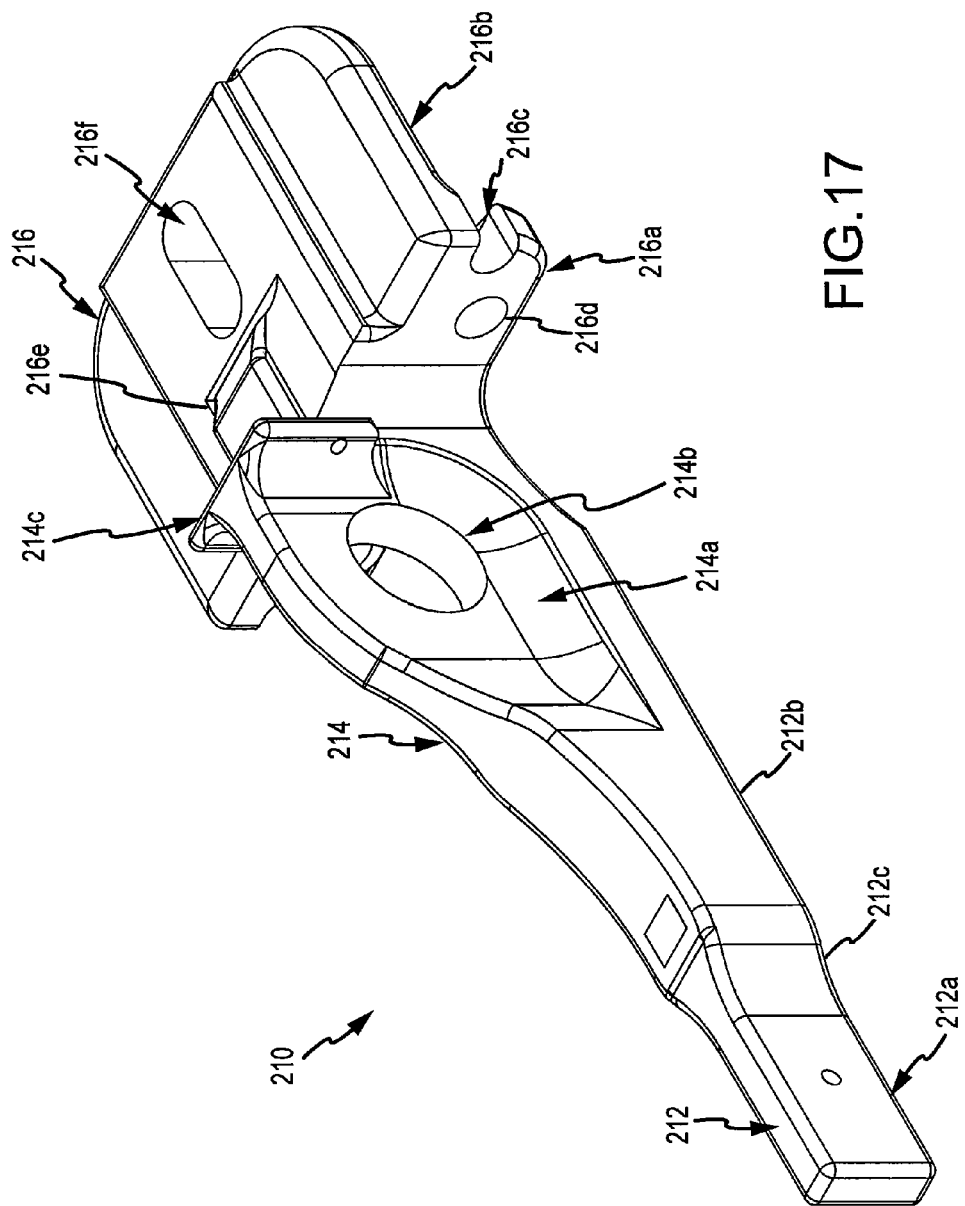
FIGS. 17-22 illustrate an embodiment of the core body of the core assembly illustrated in FIGS. 11-16.
Figure 18:
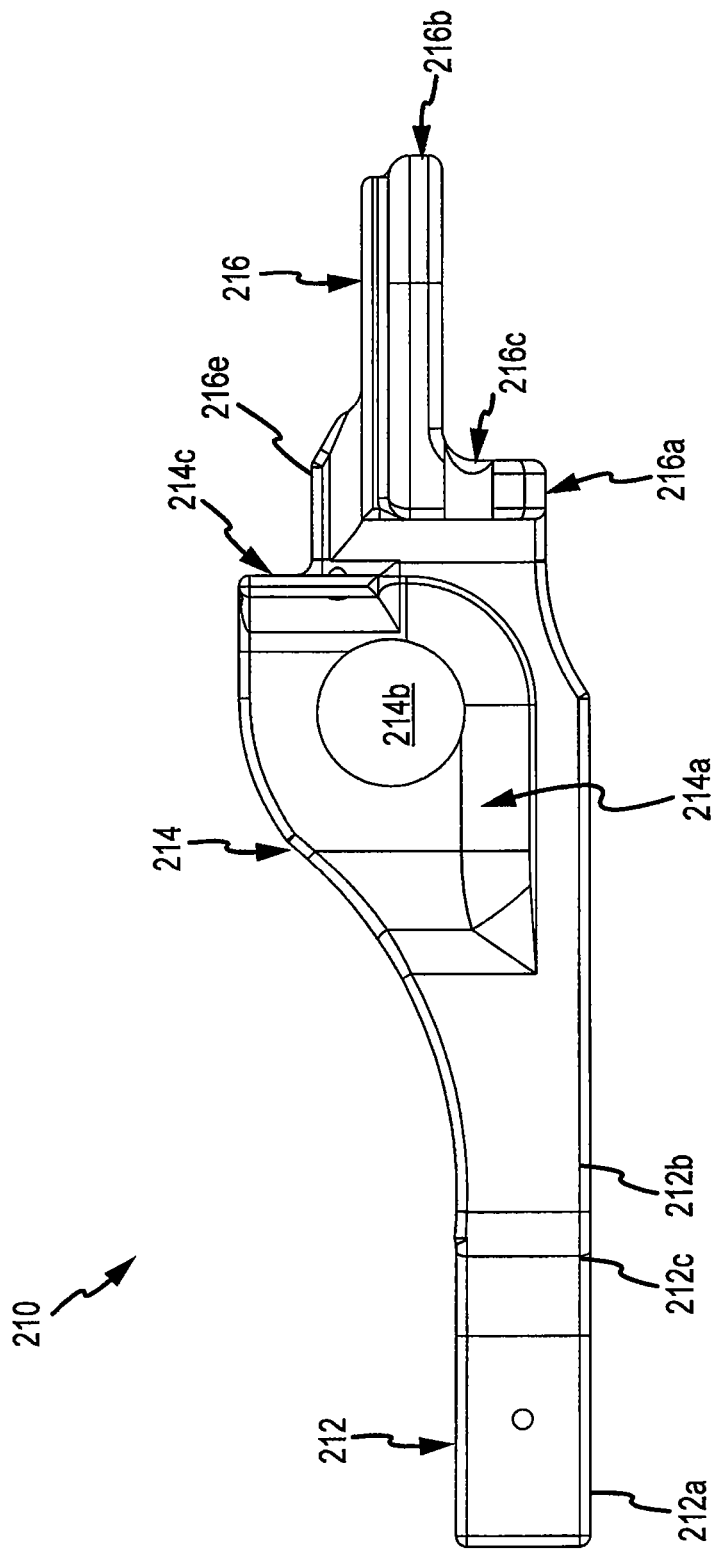
Figure 19:
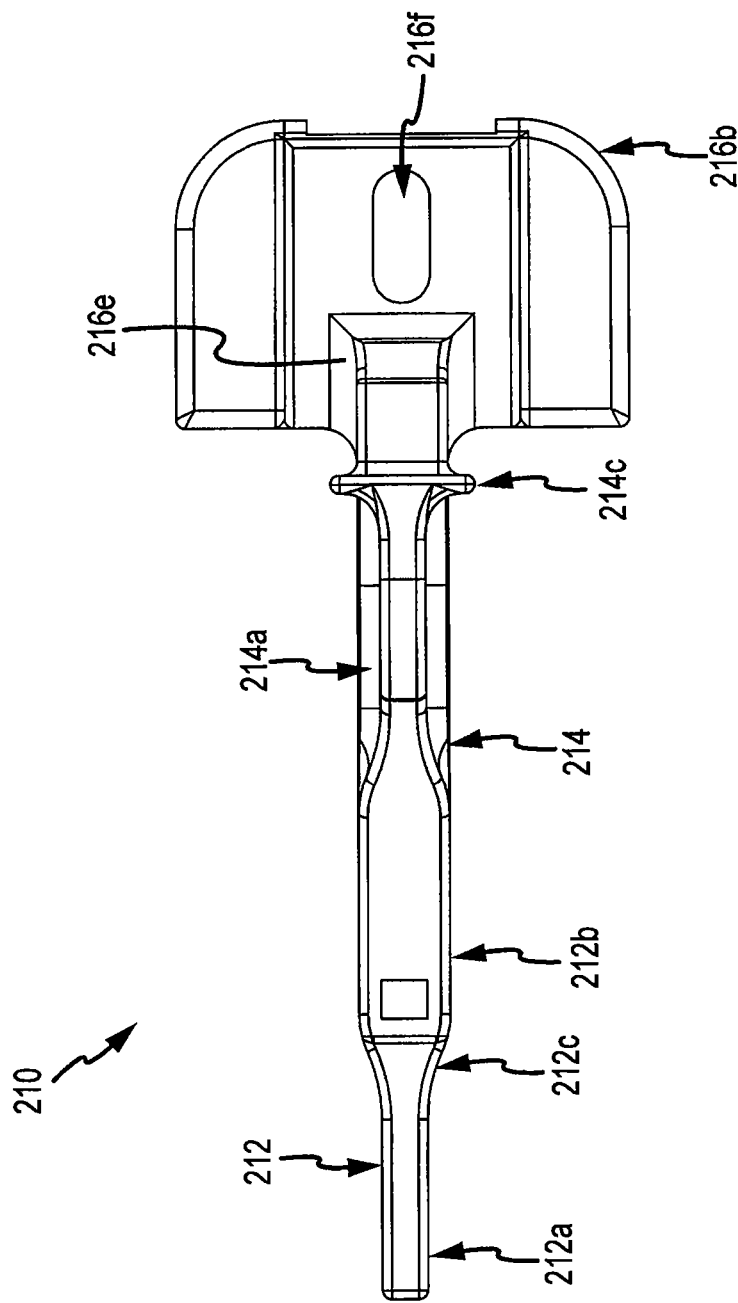
Figure 20:
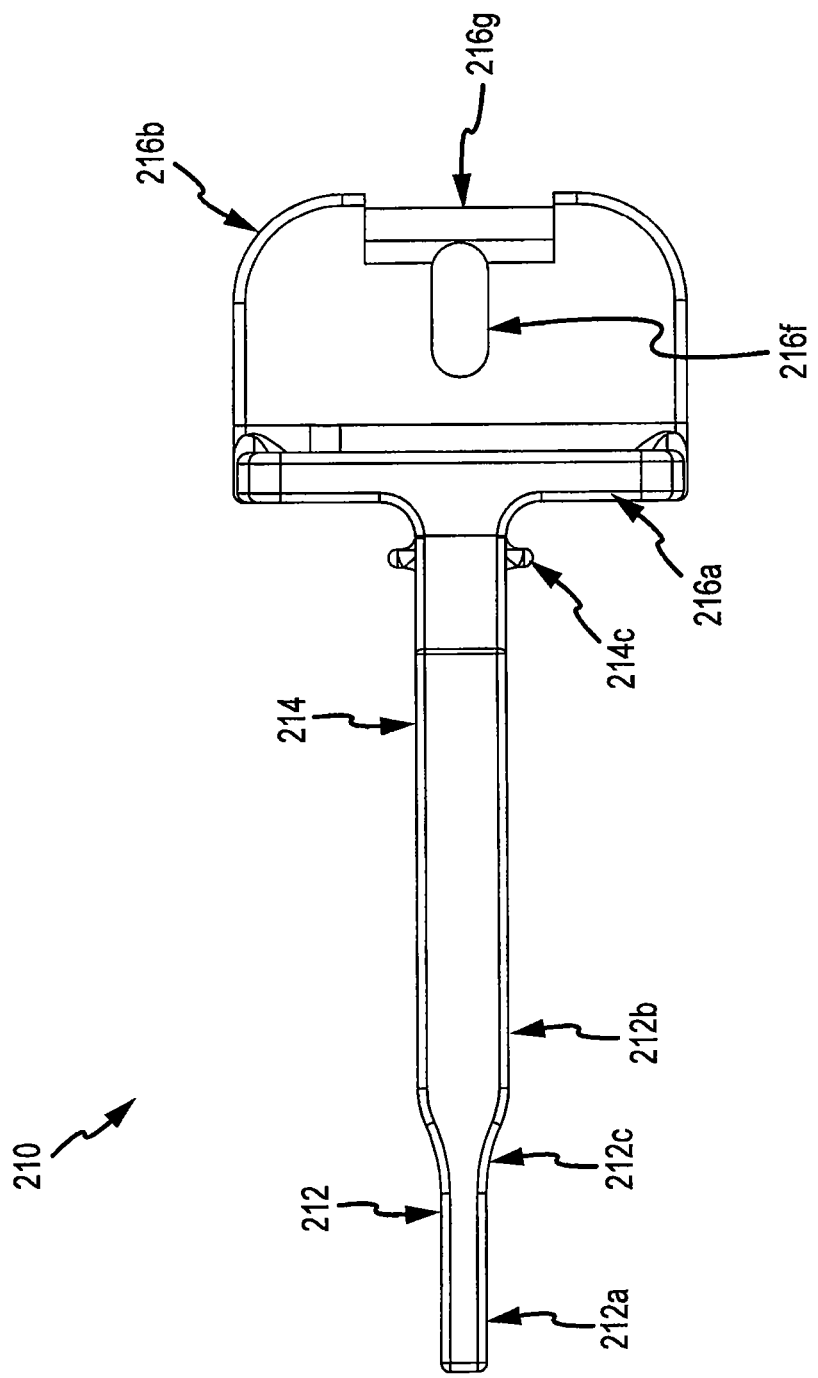
Figure 21:
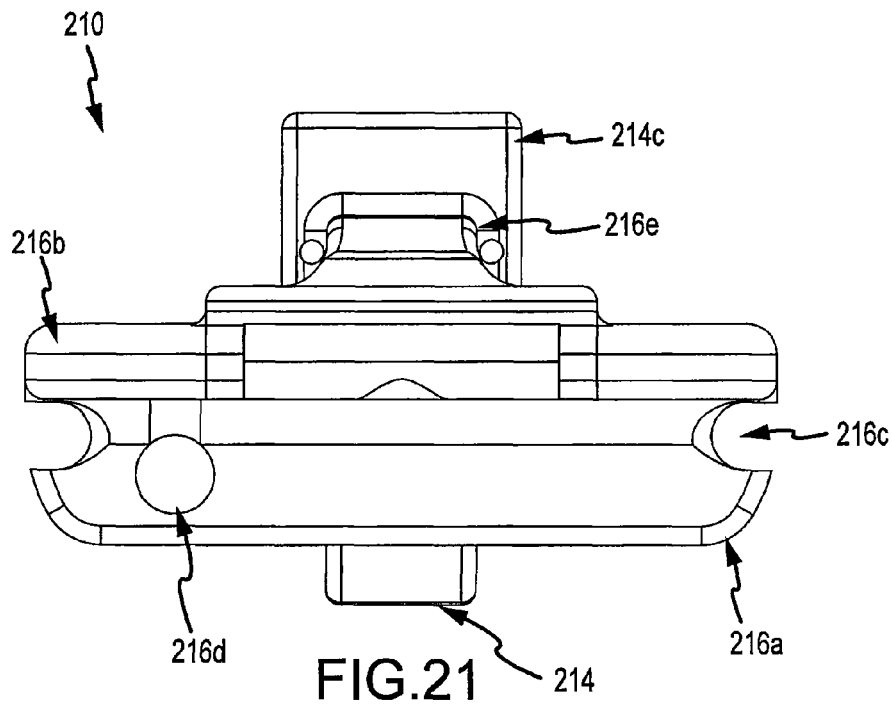
Figure 22:
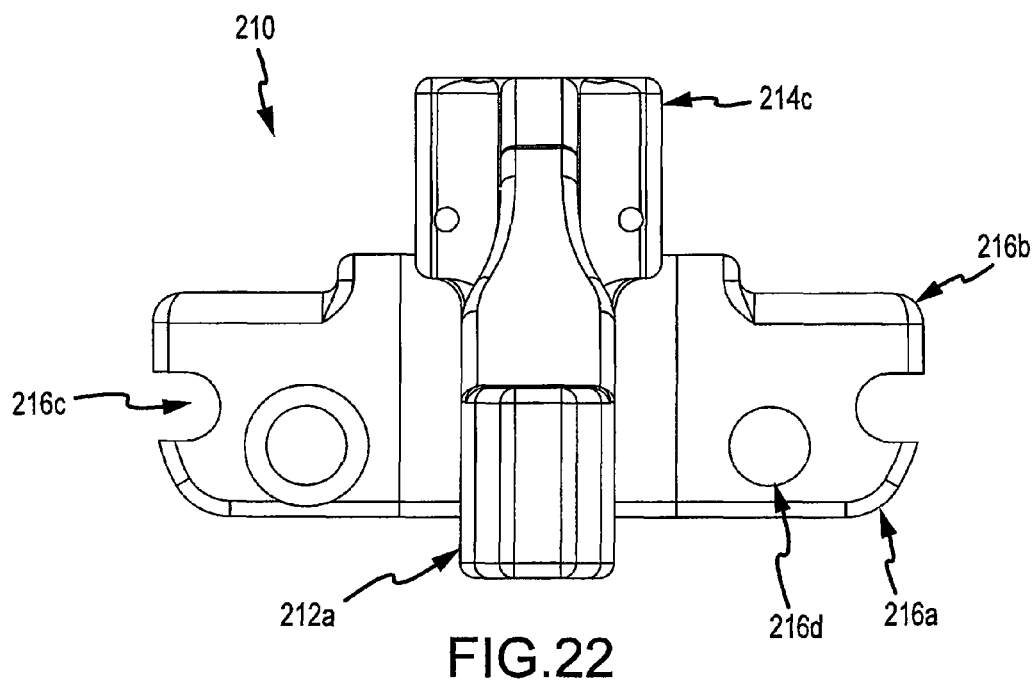

FIGS. 17-22 illustrate an embodiment of the core body 210 of the core assembly 200 illustrated in FIGS. 11-16. FIG. 17 depicts a perspective view of the core body 210. FIG. 18 depicts a right side view of the core body 210. FIG. 19 depicts a top view of the core body 210. FIG. 20 depicts a bottom view of the core body 210. FIG. 21 depicts a front view of the core body 210. FIG. 22 depicts a rear view of the core body 210.

The core body 210 may include a rear section 212, a mid-section 214 and a front section 216. The rear section 212 may include an end portion 212a, a transitional portion 212b and a tapering portion 212c between the transitional portion 212c and the end portion 212a. The end portion 212a may be rectangular, as shown, or may be any suitable shape that provides for engagement with the Achilles sheave 220, as discussed below. The tapering portion 212b may be configured to facilitate substantial alignment of the core body 210 with the Achilles sheave 220, to help prevent over insertion and/or to allow some lateral movement between the core body 210 and the Achilles sheave 220. Although not illustrated, the tapering may also be provided on the top and/or bottom to allow some vertical movement between the core body 210 and the Achilles sheave 220.

The mid-section 214 may include a narrowed or recessed portion 214a. The narrowed portion 214a may facilitate insertion of the mid-section 214 into the channel 136 between the right and left flanges 132, 134 of the talus body 100. An aperture 214b may be formed in the narrowed portion 214a. When assembled with the talus body 100, this aperture 214b of the core body 210 may receive an axle and/or bushings for an axle, as discussed below with respect to FIG. 39. The mid-section 214 may also include a flange portion 214c that includes right and left laterally extending flanges. The flange portion 214c may include holes for attachment screws (discussed below with respect to FIG. 39) that secure the mid-foot bearing 230 to the flange portion 214c. As discussed further below, the mid-foot bearing 230 may interact with the talus body 100 to limit lateral and/or twisting movement of the core body 210 relative to the talus body 100.

The front section 216 may include a substantially vertical portion 216a adjacent the mid-section 214, and a substantially horizontal portion 216b extending forwardly from the substantially vertical portion 216a. The substantially vertical portion 216a may include a third rope retaining means. The third rope retaining means may include right and left grooves 216c and a hole 216d.

The substantially horizontal portion 216b may include a raised portion 216e, for example, in the center rear thereof. As discussed further below, the raised portion 216e may be configured to locate and/or engage the mid-foot bearing 230a relative to and/or with the core body 210. The substantially horizontal portion 216b may also include a toe bracket coupling or engagement means 216f. The coupling/engagement means 216f may include an aperture extending substantially vertically through the substantially horizontal portion 216b. The aperture may be configured to receive a bolt or other fastener that may couple the substantially horizontal portion 216b of the core body 210 with the toe bracket 240, as discussed below.

As shown in FIG. 20, the substantially horizontal portion 216b may include a cutout 216g. The cutout 216g may be progressive or stepped, and may be configured to allow movement of the toe 300 within the toe bracket 240 when the toe bracket 240 is coupled to the substantially horizontal portion 216b of the core body 210. The cutout 216g may also provide space for a tension rope extending between the toe 300 and the toe bracket 240, as discussed further below.

FIGS. 23-28 illustrate an embodiment of the Achilles sheave 220 of the core assembly 200 illustrated in FIGS. 11-16. FIG. 23 depicts a perspective view of the Achilles sheave 220. FIG. 24 depicts a left side view of the Achilles sheave 220. FIG. 25 depicts a top view of the Achilles sheave 220. FIG. 26 depicts a bottom view of the Achilles sheave 220. FIG. 27 depicts a front view of the Achilles sheave 220. FIG. 28 depicts a rear view of the Achilles sheave 220.

The Achilles sheave 220 may include a raised top portion 222. The raised top portion may be configured to correspond with the recess 118 formed in the rear portion 110 of the talus body 100. For example, the raised top portion 222 and the recess 118 may be complementary such that the raised top portion 222 fits at least partially within the recess 118 during relative movement of the talus body 100 and the core assembly 200. The raised top portion 222 may also provide a stop that limits the relative movement of the talus body 100 and the core assembly 200 by contacting the bottom of the talus body 100 or the cushioning material within the recess 118.

The Achilles sheave 220 may include an extended portion 224 that extends rearwardly beyond the raised top portion 222. A rear flange or flanges 224a may be disposed on the extended portion 224 to help retain a tension rope, as discussed further below with respect to FIGS. 50-56. For example, the flange(s) 224a may retain the tension rope between the flange(s) 224a and the raised top portion 222.

The Achilles sheave 220 may also include a rearwardly extending bottom flange 226. The bottom flange 226 may define a space 226a between the bottom flange and the extended portion 224 for receiving a tension rope, as discussed further below. The bottom flange 226 may also provide a resilient impact member for absorbing heel strike of the artificial foot 10 during use.

As shown in FIG. 27, the Achilles sheave 220 may include an aperture 228 configured to receive the rear section 212 of the core body 210. The aperture 228 may be complementary to the shape of the rear section 212. For example, the aperture 228 may be rectangular and may or may not be tapered. Thus, it should be understood that the aperture 228 and/or the rear section 212 may be shaped to cooperate to couple the Achilles sheave 220 with the core body 210 with or without a limited amount of lateral and/or vertical relative movement, as appropriate or desired. In one embodiment, the Achilles sheave 220 is fixedly secured to the core body 210, such that the Achilles sheave 220 and the core body 210 move together as an assembly, without any relative movement.

FIGS. 29-33 illustrate an embodiment of the mid-foot bearing 230 of the core assembly 200 illustrated in FIGS. 11-16. FIG. 29 depicts a perspective view of the mid-foot bearing 230. FIG. 30 depicts a right side view of the mid-foot bearing 230. FIG. 31 depicts a top view of the mid-foot bearing 230. FIG. 32 depicts a bottom view of the mid-foot bearing 230. FIG. 33 depicts a front view of the mid-foot bearing 230.

The mid-foot bearing 230 may be configured as a substantially U-shaped member both horizontally and vertically. As shown in FIG. 33, the mid-foot bearing 230 may include right and left downward extensions 232 and a lateral section 234. The downward extensions 232 and the lateral section 234 may define a space 232a between the extensions 232. A rear recess 236 may be formed in the lateral section 234. The rear recess 236 may be dimensioned to receive the flange portion 214c of the core body 210, which may facilitate locating the mid-foot bearing 230 during assembly and may provide structural engagement between the core body 210 and the mid-foot bearing 230. Such engagement may enhance the attachment of the mid-foot bearing to the flange portion 214c, discussed below with respect to FIG. 39. The mid-foot bearing 230 may be configured to interact with the talus body 100 to limit an amount of lateral and/or twisting movement of the core assembly 200 relative to the talus body 100. As appropriate or desired, the rear recess 236 may extend into the downward extensions 232, either partially or entirely as shown. Further, the downward extensions 232 may be radiused or chamfered at the sides and/or bottom. The radius/chamfer at the bottom of the downward extensions 232 may facilitate assembly, for example, by making it easier to position the mid-foot bearing 230 between the talus body 100 and the core body 210. The radius/chamfer at the sides of the downward extensions 232 may provide a suitable surface for contacting the talus body 100 during movement, for example, avoiding an edge contact and/or loading between the mid-foot bearing 230 and the talus body 100. Further, a horizontal groove 238 may be formed in the lateral section 234 for receiving and retaining a tension rope extending between the mid-foot bearing 230 and the talus body 100, as discussed below with respect to FIGS. 49-55. The groove 238 may be formed in the front and/or the sides of the lateral section 234, as appropriate or desired.

FIGS. 34-38 illustrate an embodiment of the toe bracket 240 of the core assembly 200 illustrated in FIGS. 11-16. FIG. 34 depicts a perspective view of the toe bracket 240. FIG. 35 depicts a right side view of the toe bracket 240. FIG. 36 depicts a top view of the toe bracket 240. FIG. 37 depicts a bottom view of the toe bracket 240. FIG. 38 depicts a front view of the toe bracket 240.

The toe bracket 240 may be configured as a substantially U-shaped member horizontally with right and left forward extensions 242. Each of the extensions 242 may include a rope retaining means for toe ropes that extend between the toe bracket 240 and the toe 300. Each rope retaining means may include a groove 242a and a recess 242b that opens into the groove 242a. The recesses 242b may be of any suitable shape depending on the shape of the connector or stop at the ends of the respective toe ropes. For example, the recesses 242b may be substantially cylindrical to receive and retain cylindrical, spherical or semi-spherical connectors. As illustrated, the recesses 242a may include a curved surface or bend radius, protecting the toe ropes from damage from an edge or sharp angle bend. Further, the curved surface or bend radius may be paralleled by the forward extensions 242 to provide a rolling contact surface, as described further below.

The toe bracket 240 may include a core body engagement means 244. Similar to the coupling/engagement means discussed above with respect to the core body 210, the core body engagement means 244 may include a substantially vertical aperture 244a extending through the toe bracket 240. The aperture 244a may include a peripheral recess, as appropriate or desired, for receiving a star washer to resist rotation of the toe bracket 240 relative to the core body 210 when assembled, as discussed below with respect to FIG. 39. The core body engagement means 244 may also include a bottom recess 244b, which may be of any suitable shape to receive and retain a connector, such as a nut when a bolt extends through the substantially vertical aperture 244a and the hole 216f in the core body 210 to couple the toe bracket 240 with the core body 210.

The toe bracket 240 may include another toe rope retaining means 246. The toe rope retaining means 246 may be formed in a top of the toe bracket 240, for example, along a centerline of the toe bracket 240. The toe rope retaining means 246 may include a groove 246a that opens to the front of the toe bracket 240 and a recess 246b configured to receive and retain a connector or stop at the end of the toe rope. The recess 246b may be of any suitable shape, and may be offset, as shown, to provide room for the aperture 244a.

The toe bracket 240 may also include an external horizontal groove 248. The groove 248 may be relatively wide to receive multiple windings of a tension rope. Another rope retaining means, such as a hole 248a, may be included in the toe bracket 240 so that one end of the rope retained in the groove 248 may be secured to the toe bracket 240 and the other end may be secured to the core body 210, for example, via the hole 216d. It should be understood that both ends of such rope may be secured to the core body 210 or to the toe bracket 240, as appropriate or desired.

Figure 39:
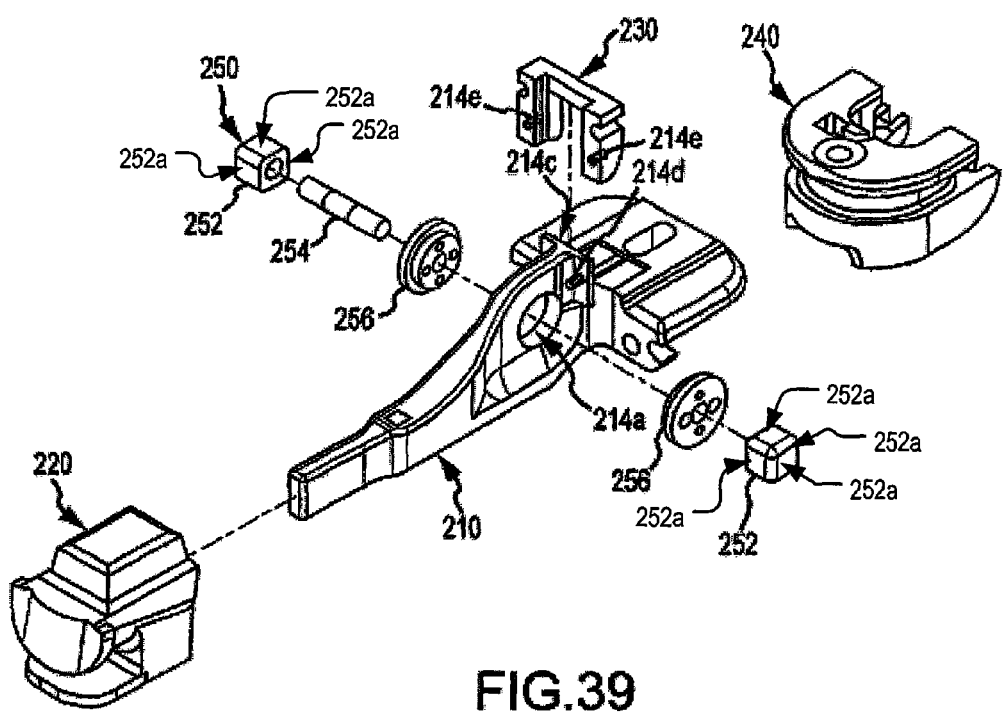
FIG. 39 illustrates an exploded view of the core assembly illustrated in FIGS. 11-16.

FIG. 39 illustrates an exploded view of the core assembly 200 illustrated in FIGS. 11-16. In addition to the core body 210, the Achilles sheave 220, the mid-foot bearing 230 and the toe bracket 240, the core assembly 200 may include a pivot bearing assembly 250. The pivot bearing assembly 250 may include right and left pivot bearings 252, each pivot bearing including bearing surfaces 252a. The pivot bearings 252 may be configured to be seated in the bearing recesses 132b and 134b of the talus body 100. As discussed above, there may be some play (longitudinal, lateral and/or vertical for the pivot bearings 252 when seated in the bearing recesses 132b, 134b. The pivot bearings 252 may also be configured to support an axle 254 that passes through the aperture 214a in the mid-section 214 of the core body 210. The axle 254 may be coupled with the core body 210 at the aperture 214a via right and left bushings 256. The bushings 256 may be configured to prevent "wallering" or ovalization of the hole 214a through the core. As the axle 254 may be made from a material that is harder than the material of the core body 210, the bushings 256 may be made of a sufficiently hard material to prevent "wallering" that otherwise may occur due to relative movement of axle 254 relative to the core body 210. The axle 254 may be fixedly secured to the core body 210 via the bushings 256, and may be allowed to rotate relative to the pivot bearings 252. Thus, this arrangement may allow the talus body 100 and the core body 210 to pivot relative to one another; and, as appropriate or desired, the pivot bearings 252 may also allow some lateral, vertical and/or twisting movement of the core body 210 relative to the talus body 100, as constrained by contact of the mid-foot bearing 230 with the talus body 100 and the interaction of the pivot bearing with the lateral walls of the pivot bearing recesses. Vertical motion may be constrained by the bearing recesses. The mid-foot bearing may be fixedly connected to the flange portion 214c of the core body 210, for example, by screws 214d, which may fit through threaded bores (unnumbered) in the flange portion 214c. The mid-foot bearing 230 may include corresponding holes 214e for receiving the screws 214d. Alternatively, the screws 214d may be self-tapping, avoiding the need for bores/holes and/or any need for exact placement of the screws 214d. For example, indentations in the flange portion 214c may be sufficient to guide self tapping screws to secure the mid-foot bearing 230 once in place. A fixed connection of the Achilles sheave 220 to the core body 210 may be provided by any suitable means, such as a fastener, glue, welding and the like, depending on the materials used for the Achilles sheave 220 and the core body 210. As discussed above, the toe bracket 240 may also be fixedly connected with the core body 210 by the connection means described, or in any other suitable manner.

FIGS. 40-45 illustrate an embodiment of the toe 300 of the artificial foot 10 illustrated in FIGS. 1-4. FIG. 40 depicts a perspective view of the toe 300. FIG. 41 depicts a left side view of the toe 300. FIG. 42 depicts a top view of the toe 300. FIG. 43 depicts a bottom view of the toe 300. FIG. 44 depicts a front view of the toe 300. FIG. 45 depicts a rear view of the toe 300.

The toe 300 may include a rear section 302 and a front section 304. The rear section 302 may include a lateral aperture 302a for receiving a toe race (not shown), discussed below with respect to FIGS. 46-49. The rear section 302 may also include a longitudinal groove 302b. The groove 302b may extend over at least a top portion of the rear section 302, for example, for receiving a toe rope as described further below.

The front section 304 of the toe 300 may include a relatively wide front end 306, which may provide suitable stability for toe push-off during use. The front section 304 may taper from the front end 306 to the rear section 302, and thus may be substantially triangular. Although not shown, the front section 304 of the toe 300 may be configured as a triangular frame, for example, to reduce weight while retaining structural strength.

At outer edges of the front end 306, grooves 306a and recesses 306b opening rearwardly to the grooves 306a may be provided to form first and second toe rope retaining means. A third toe rope retaining means 308 may be formed by a hole 308a aligned with the groove 302b and opening into a recess 308b in a bottom of the toe 300. The first, second and third toe rope retaining means thus defined may be configured to retain tension ropes that couple the toe 300 with the toe bracket 240. As discussed further below, the other ends of such tension ropes may be secured to the toe bracket 240 via the toe rope retaining means discussed above with respect to the toe bracket 240.

Figure 46:
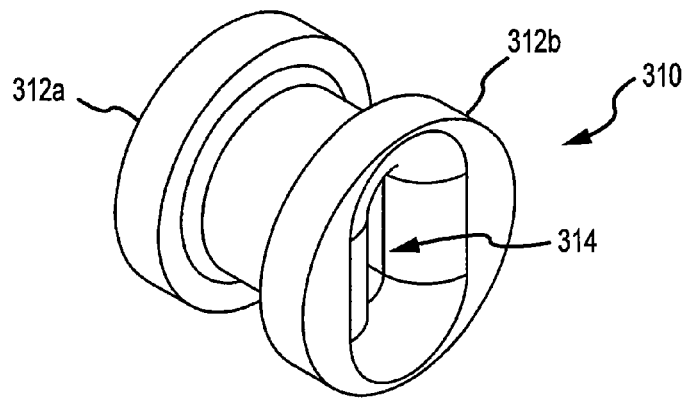
FIGS. 46-48 illustrate an embodiment of a toe race for the toe illustrated in FIGS. 40-45.
Figure 48:
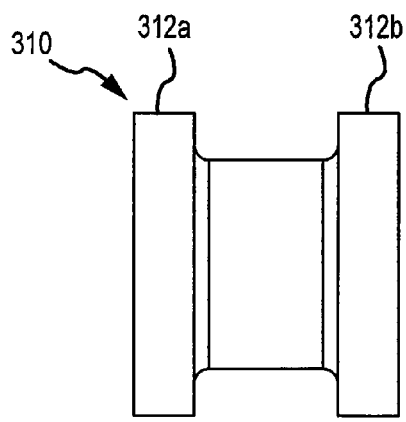
Figure 47:
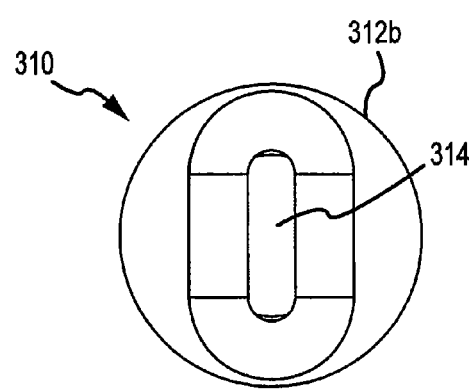

FIGS. 46-48 illustrate an embodiment of a toe race 310 for the toe 300 illustrated in FIGS. 40-45. FIG. 46 depicts a perspective view of the toe race 310. FIG. 47 depicts a side view of the toe race 310. FIG. 48 depicts a front/rear view of the toe race 310.

The toe race 310 may be substantially cylindrical with left and right flanges 312a and 312b. The toe race 310 may be configured to fit within the aperture 302a of the toe 300, with the flanges 312a and 312b serving to retain the toe race 310 therein while allowing rotation of the toe 300 relative to the toe race 310. As described herein, the flanges 312a and 312b may be configured to limit relative motion between the toe 300 and the core body 200 by contacting the toe bracket 14 during relative lateral and/or twisting motions. Thus, the flanges 312a, 312b, or the entire toe race 310 may be made of a suitable material, such as a plastics material, to absorb the impact of such contact. The toe race 310 may include a lateral aperture 314 configured to receive a tension rope that may be wound about the toe bracket 240 several times. Thus, the aperture 314 may be oblong to accommodate multiple windings of the rope.

Figure 49:
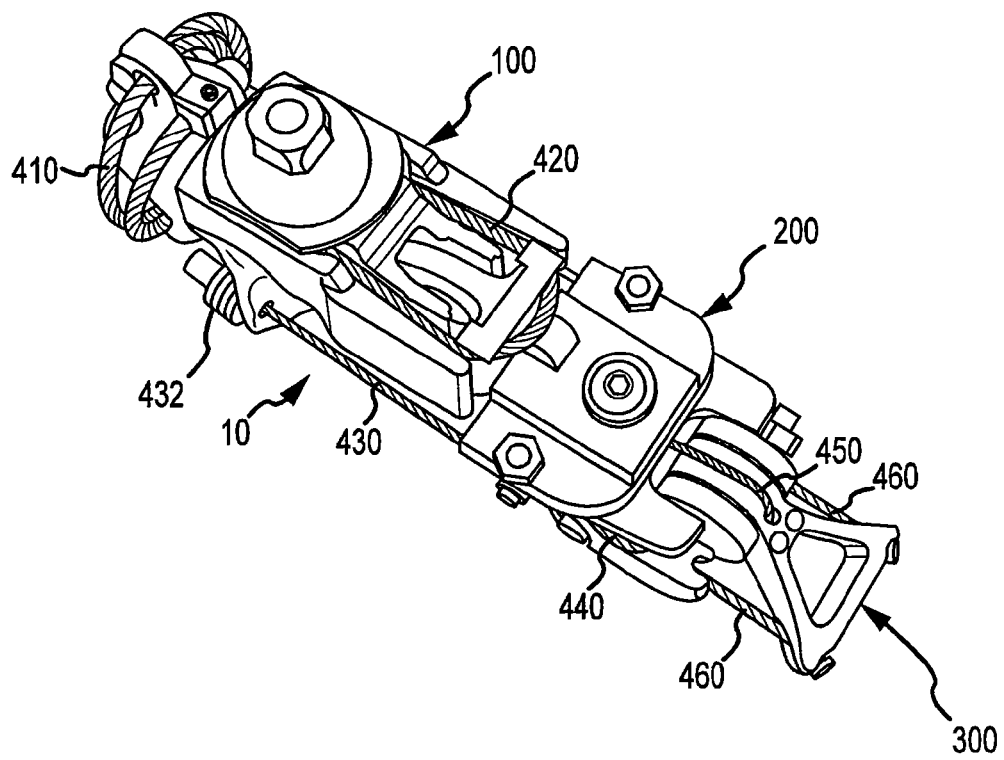
FIGS. 49-55 illustrate an embodiment of the artificial foot illustrated in FIGS. 1-4 including tension ropes.
Figure 50:
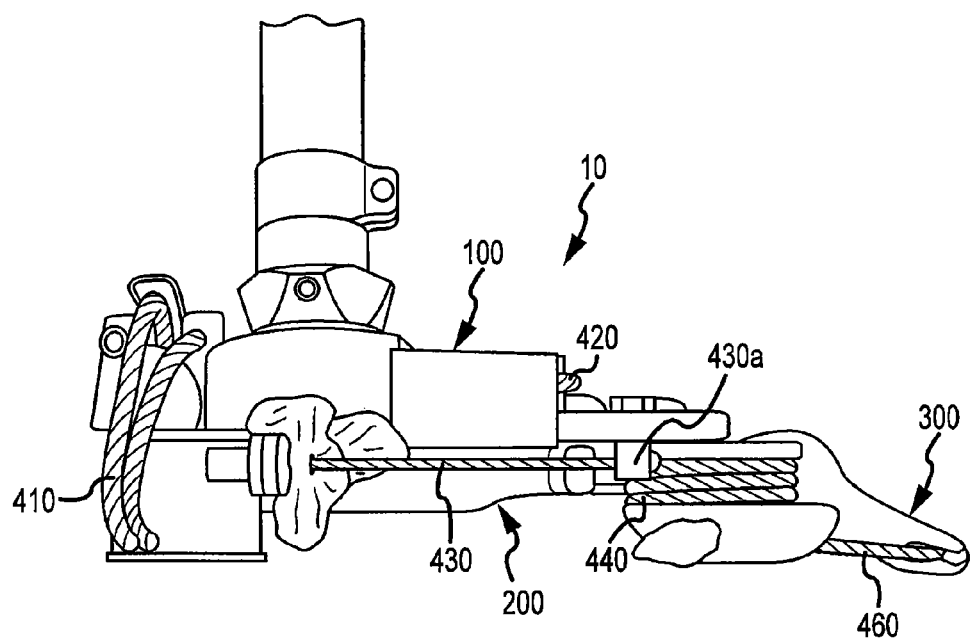
Figure 51:
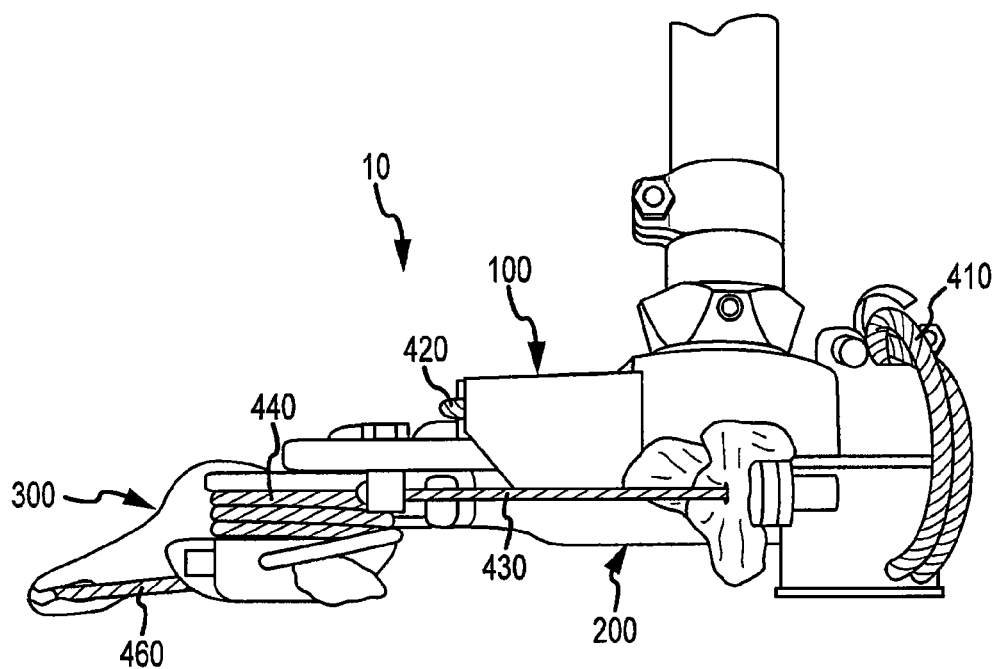
Figure 52:
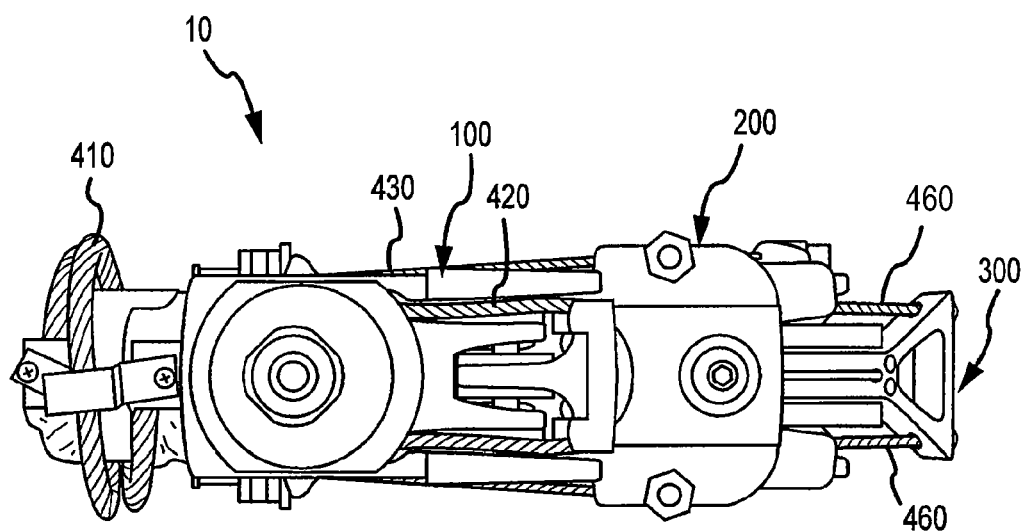
Figure 53:
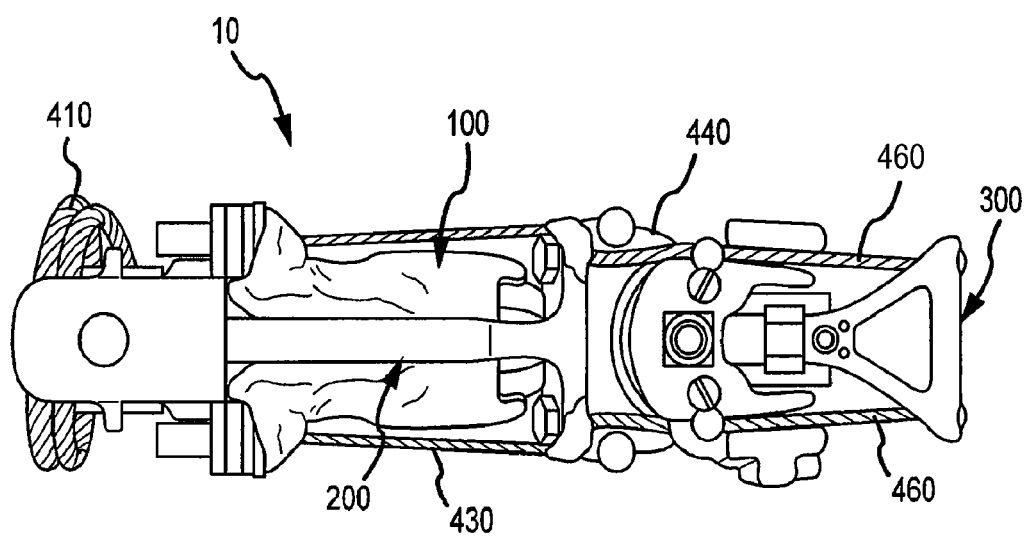
Figure 54:
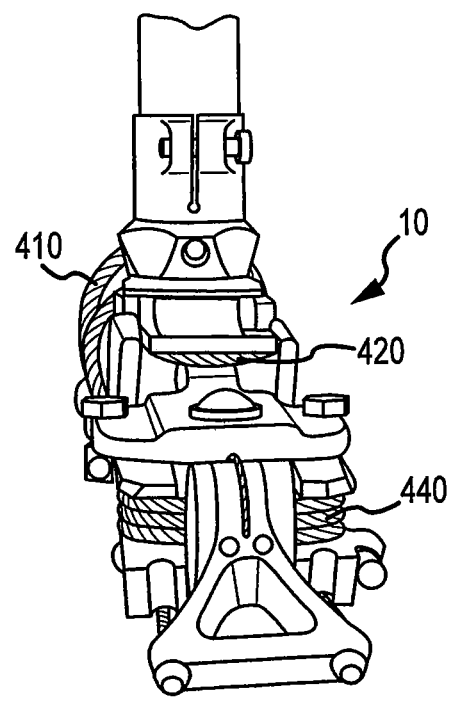
Figure 55:
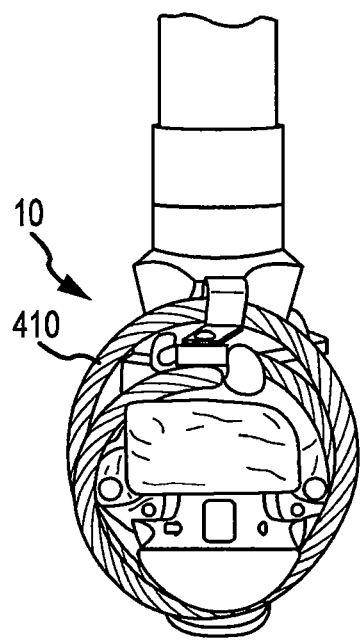

FIGS. 49-55 illustrate an embodiment of the artificial foot 10 illustrated in FIGS. 1-4 including tension ropes. FIG. 49 depicts a perspective view of the artificial foot 10. FIG. 50 depicts a right side view of the artificial foot 10. FIG. 51 depicts a left side view of the artificial foot 10. FIG. 52 depicts a top view of the artificial foot 10. FIG. 53 depicts a bottom view of the artificial foot 10. FIG. 54 depicts a front view of the artificial foot 10. FIG. 55 depicts a rear view of the artificial foot 10.

Various tension ropes may be included to implement the joints generally indicated by reference numerals 12 and 14. These joints 12 and 14 help define the functional interrelationships between the movable structures of the artificial foot 10 and contribute to a more realistic and effective walking dynamic for the artificial foot 10.

As shown in FIGS. 49-55, a rear tension rope 410 may be employed to couple the Achilles sheave 220 with the talus body 100. Specifically, the rear tension rope 410 may be secured at one end to the protrusion 114a of the talus body 100, wrapped around the rear section 110 of the talus body 100 and the rearwardly extending body portion 224a of the Achilles sheave 220 one or more times and then secured at the other end to the protrusion 114b of the talus body 100.

The rear tension rope 410 may thus limit a distance apart that the Achilles sheave 220 and the talus body 100 may move during use (e.g., under load during walking movement). The rear tension rope 410 may also limit relative movement of the other structures of the core assembly 200 because of the connection between the end portion 212a and the aperture 228 of the Achilles sheave 220. The rear tension rope 410 may thus provide constraints on relative movement for the joint 12.

It should be noted that the rear section 110 of the talus body 100 and the rearwardly extending body portion 224a of the Achilles sheave 220 may be rounded to help prevent damage to the rear tension rope 410 from these structures, and vice versa. Further, it should be noted that the protrusions 114a, 114b, the rear flange 116 and the flange(s) 224a also may help prevent damage by maintaining the rear tension rope 410 in place about the Achilles sheave 220 and the rear section 110 of the talus body 100.

An upper tension rope 420 may be employed to couple the talus body 100 with the mid-foot bearing 230 of the core assembly 200. Specifically, the upper tension rope 420 may be secured at one end to the mid-section 120 of the talus body 100 via one of the recesses 122b, extended through the corresponding grooves 122a and 132a/134a, the horizontal groove 238 of the mid-foot bearing 230 and the other grooves 122a and 134a/132a, and then secured at the other end to the mid-section 120 of the talus body 100 via the other of the recesses 122b. The grooves 122a and 132a/134a may be configured to avoid damaging the upper tension rope 420 during movements of the artificial foot 10.

The upper tension rope 420 may thus limit a distance apart that the talus body 100 and the mid-foot bearing 230 may move during use. Thus, the upper tension rope 420 may limit relative movement between the talus body 100 and the core 200 in combination with the interaction/contact of the mid-foot bearing 230 with the right and left flanges 132, 134 of the talus body 100 (described above with respect to FIGS. 5-10. Accordingly, the upper tension rope 420 may thus provide additional constraints on relative movement for the joint 12.

A longitudinal tension rope 430 may be employed to couple each of the downward extensions 124 of the talus body 100 with the front section 216 of the core body 210. Specifically, the longitudinal tension ropes 430 may pass through a respective one of the grooves 216*c* and may be secured at one end to a respective post connector 430*a*, which may be attached to the front section 216 of the core body 210. Alternatively, these ends of the tension rope 230 may be secured to the substantially vertical portion 216*b* of the front section 216 of the core body 210. The ropes 430 may be secured at the other end to a respective one of the extensions 124. As illustrated, one or more spring washers 432 may be used to couple the longitudinal tension ropes 430 with the downward extensions 124. As described herein, the spring washers 432 may provide resilient extension for the tension ropes 430 during movements of the artificial foot 10. The spring washers 432 may be replaced by coil springs or any other suitable elastic members. During movement, the spring washers 432 may elastically deform to provide some resistance to relative movement between the talus body 100 and the core 200, particularly during heel lift.

The longitudinal tension ropes 430 may thus limit a distance apart that the talus body 100 and the core body 210 may move during use. In particular, the longitudinal tension ropes 430 may limit relative longitudinal movement of the talus body 100 relative to the core 200. Thus, the longitudinal tension ropes 430 may thus provide additional constraints on relative movement for the joint 12.

Another tension rope 440 may be employed to couple the toe bracket 240 with the toe 300. Specifically, the tension rope 440 may be secured at one end to either the substantially vertical portion 216*b* of the front section 216 of the core body 210 via the hole 216*d* or the toe bracket 240 itself, and secured at the other end to either the toe bracket 240 via the hole 248*a* or the front section 216 of the core body 210, with multiple wraps through the horizontal groove 248 and the lateral aperture 314 of the toe race 310.

The tension rope 440 may thus limit a distance apart that the toe 300 and the toe bracket 240 may move during use. In particular, the tension rope 440 may limit longitudinal movement of the toe 300 relative to the toe bracket 240, and thus relative to the core assembly 200 to which the toe bracket 240 is coupled. The tension rope 440 may thus provide constraints on relative movement for the joint 14. As shown, the joint 14 may be a tensegrity joint.

A first toe tension rope 450 may be employed to further couple the toe 300 with the toe bracket 240. Specifically, the first toe tension rope 450 may be secured at one end to the toe bracket 240 via the groove 246*a* and the recess 246*b*, and secured at the other end to the toe 300 via the groove 302*b*, the hole 308*a* and the recess 308*b*.

The first toe tension rope 450 may thus limit a degree of downward rotation that the toe 300 may experience during use. The first toe tension rope 450 may thus provide an additional constraint on relative movement for the tensegrity joint 14.

Second and third toe tension ropes 460 may be employed to further couple the toe 300 with the toe bracket 240. Specifically, the second and third toe tension ropes 460 may be secured at one end to the toe bracket 240 via the grooves 242*a* and the recess 242*b*, and secured at the other end to the toe 300 via the grooves 306*a* and the recesses 306*b*.

The second and third toe tension ropes 460 may thus limit a degree of upward rotation that the toe 300 may experience during use. The second and third toe tension ropes 460 may also limit an amount of lateral movement that the toe 300 may experience relative to the toe bracket 240, and thus relative to the core assembly 200 coupled thereto. The second and third toe tension ropes 460 may thus provide additional constraints on relative movement for the tensegrity joint 14.

The constraints provided by the various tension ropes may not only influence motion of the joints 12 and 14, but also may stabilize the joints 12 and 14. Moreover, as appropriate or desired, the tension ropes may be configured to store and release energy during walking movements of the artificial foot 10, thereby mimicking performance characteristics of the human foot.

By employing grooves for the tension ropes, the tension ropes may be maintained in proper place and may be less likely to be damaged. Although not specifically depicted in the drawings for the sake of simplicity, it should be understood that means for adjusting the tension of the various tension ropes may be included in a practical implementation. Any suitable adjustment mechanism may be employed.

The bottom of the Achilles sheave 220, the bottom of the toe bracket 240 and the bottom front edge of the toe 300 may serve as load-bearing surfaces during walking movements of the artificial foot 10. The loads may be efficiently transferred through the joints 12 and 14 to provide a more realistic walking performance of the artificial foot 10.

It should be noted that for each of the cables secured to a respective member by a ball-end, as illustrated in some of the figures, a bushing made of a suitable material, such as a plastics material, may be included to provide a suitable surface for movement of the ball relative to the respective member. This may facilitate smooth movement of the corresponding ropes and/or prevent wear at the rope connections. This may also apply to the post connector 430*a* shown in FIG. 50.

It should also be noted that the tensegrity joint 14 depicted for the toe 300 may be replaced by a non-tensegrity joint. For example, if the longitudinal rotation of the toe 300 relative to the core body 210 is sufficiently limited, an axle may replace the wrapping cable 440.

Operation of the artificial foot 10 during walking movement may be described as follows. Beginning with heel strike, the rear flange 226 of the Achilles sheave 220 may absorb impact and protect the rear tension rope 410. The talus body 100 may move downward toward the Achilles sheave 220, with cushioning material (when provided) in the recess 118 of the talus body 100 contacting the top portion 222 of the Achilles sheave 220 to absorb the heel strike. The talus body 100 may rotate (counter-clockwise in FIG. 50) relative to the core 200 during downward movement of the talus body 100, moving the pivot bearings 252 to a bottom of the bearing recesses 132*b*, 134*b* of the talus body 100.

The talus body 100 may then rotate about a virtual lateral axis in an opposite direction (clockwise in FIG. 50) relative to the core 200 until the artificial foot reaches a neutral (standing support) position. This rotation may be facilitated by a rebound of the Achilles sheave 220 contacting the cushioning material in the recess 118.

In the neutral position, the pivot bearings 252 may return to a top of the bearing recesses 132*b*, 134*b*. Further in this position, the artificial foot may be supported via the bottom of the Achilles sheave 220 and the bottom of the toe bracket 240 as contact/support/load-bearing surfaces.

From the neutral position, tibial progression in a forward direction causes the talus body 100 to rotate about the axle 254 of the first joint 12 via the pivot bearings 252. The longitudinal tension ropes 430 are loaded to compress the spring washers 432 while the rear tension rope 410 is tensioned. As described above, the spring washers 432 thus smooth the transition during tensioning of the rear rope 410.

With the rear tension rope 410 tensioned, continued tibial progression forward causes heel rise or lift-off. As the heel rises, the artificial foot 10 is supported by the toe bracket 240, with the forward extensions 242 providing a rolling contact surface. During this movement, the toe 300 may rotate (counter-clockwise in FIG. 50) about a lateral axis, which loads the lower toe ropes 460.

In this embodiment, the lower toe ropes 460 may have some elastic properties. Thus, the lower toe ropes 460 may be stretched by the rotation of the toe 300. One example of an elastic material for the lower toe ropes 460 is Nitinol. In such case, the stretching will be a maximum at the phase change for Nitinol. Once the limit of the lower toe ropes 460 has been reached, the artificial foot 10 may push off with the toe 300. In particular, the toe 300 may push off in a forward and upward direction, releasing energy stored in the lower toe ropes 460 in that direction as the artificial foot 10 is lifted by the user.

Figure 56:
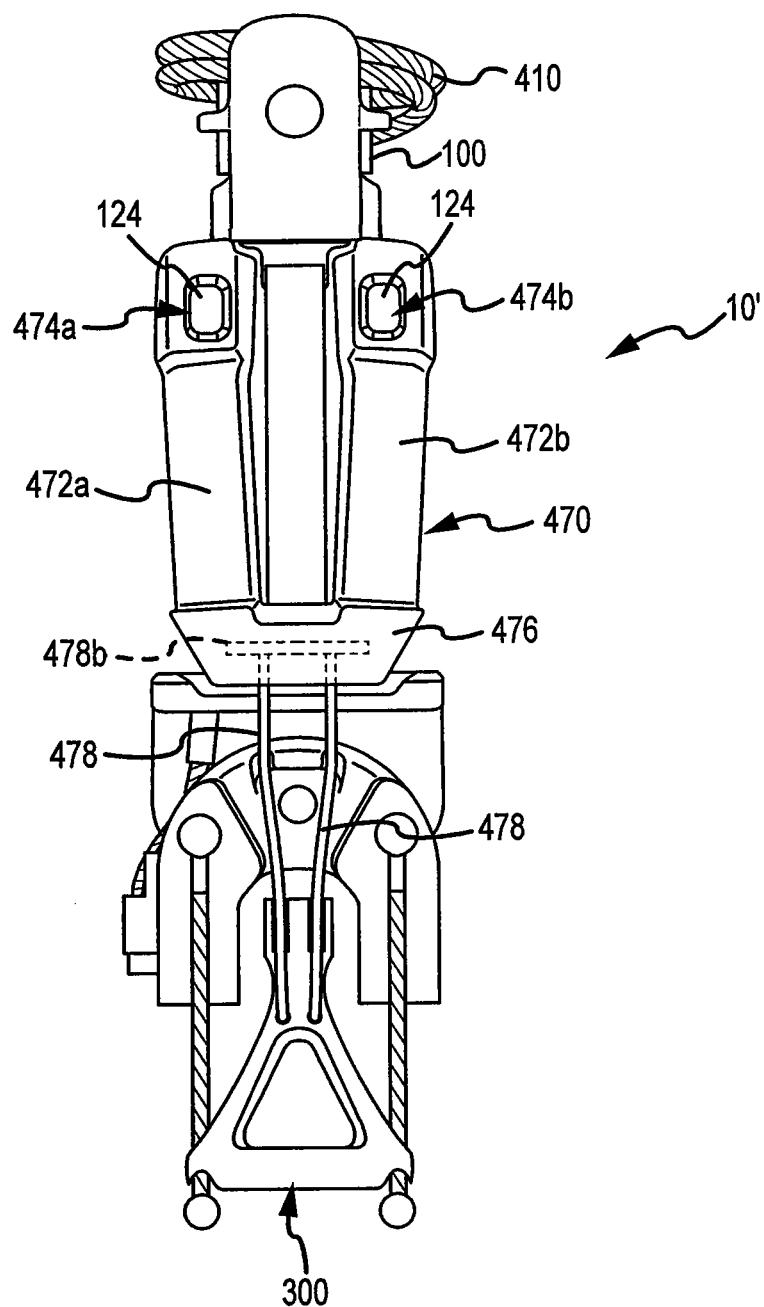
FIG. 56 illustrates a bottom view of another embodiment of an artificial foot including a coordination member.

Another embodiment of an artificial foot 10' is illustrated in FIG. 56. Similar elements in this embodiment are numbered similarly, and are not described in detail in view of the foregoing description.

Figure 57:
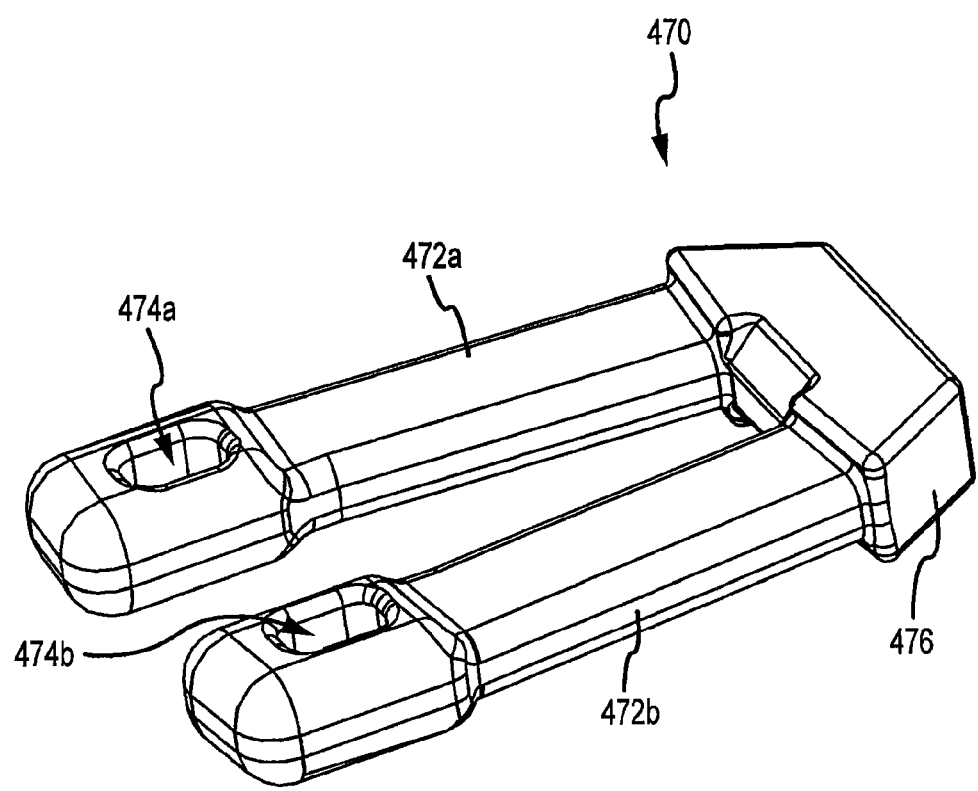
FIGS. 57-59 illustrate an embodiment of the coordination member of the artificial foot illustrated in FIG. 56.
Figure 58:
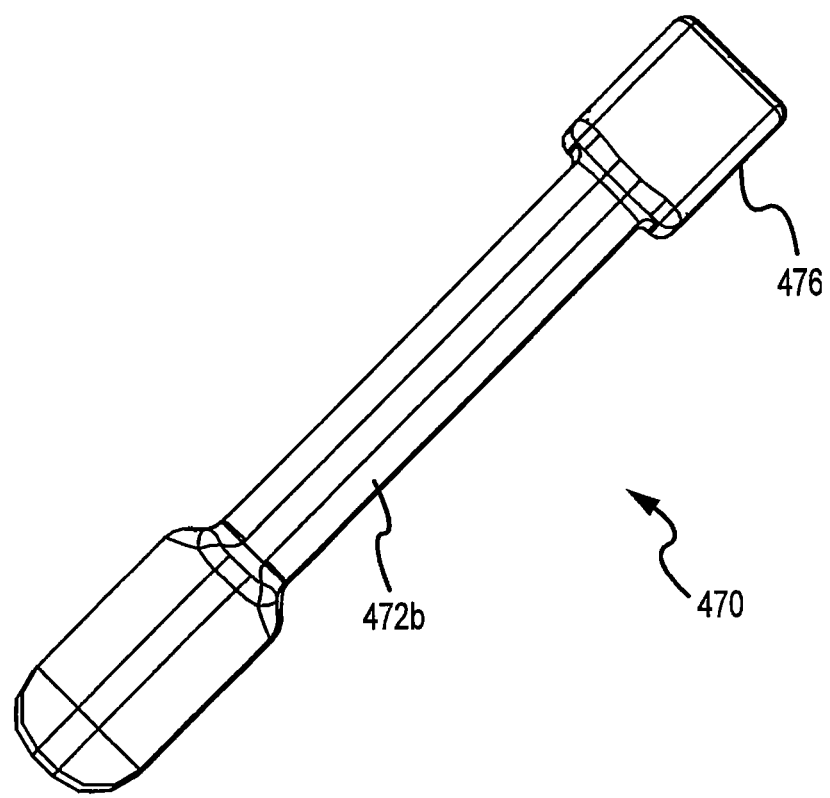
Figure 59:
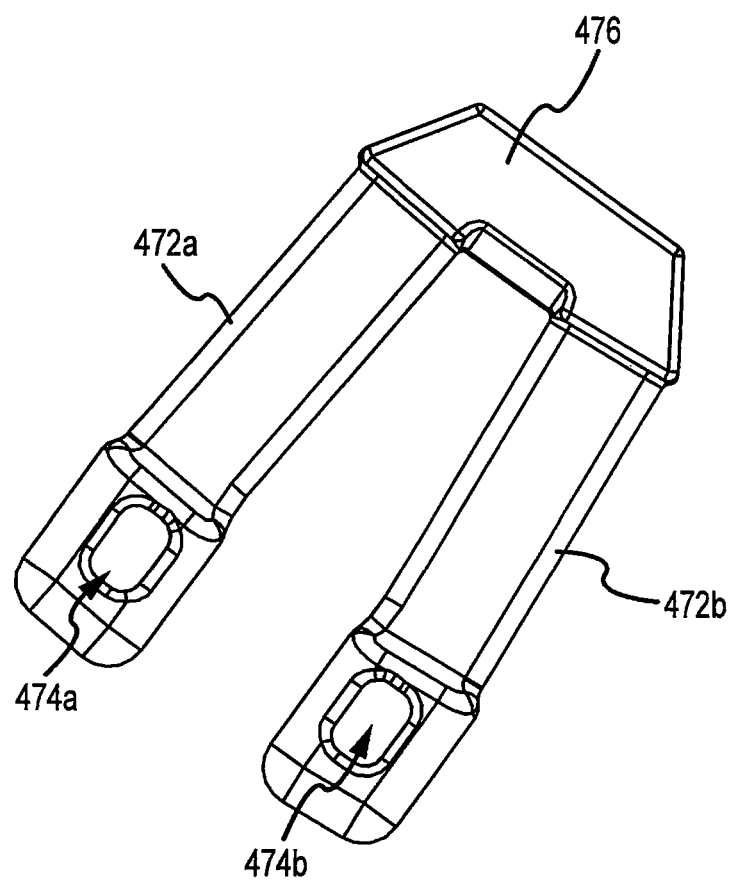

As shown in FIG. 56, and further illustrated in FIGS. 57-59, the artificial foot 10' may include a coordination member 470. The coordination member 470 may be configured to couple the talus body 100 with the toe 300. As such, the coordination member 470 may serve to coordinate the relative movements of the two joints 12 and 14.

In particular, the coordination member 470 may include left and right arm portions 472a and 472b. Respective apertures 474a and 474b may be formed in the arm portions 472a, 472b and may be configured to receive the downward protrusions 124 of the talus body 100. As appropriate or desired, the apertures 474a, 474b may or may not extend through the arm portions 472a, 472b. Further, other suitable connection or coupling between the coordination member 470 and the downward extensions 124 or other portion of the talus body 100 may be employed.

The coordination member 470 may include a front portion 476 that joins the arm portions 472a and 472b. The front portion 476 may be coupled to the toe 300. In particular, as shown the front portion 476 may be coupled to the toe 300 by one or more tension ropes 478. As shown, two or more tension ropes 478 may be employed for stability. The tension rope(s) 478 may be secured to the toe 300 in any suitable manner, such as discussed above with respect to the connections of other tension ropes to the discontinuous members of the artificial foot. For example, cylindrical or ball ends of the tension ropes 478 may be received in corresponding recesses 310 (see FIG. 1) in the toe 300.

The tension rope(s) 478 may also be secured to the coordination member 470 in any suitable manner. As illustrated, an anchor member 478b secured to the tension rope(s) 478 may be secured to the coordination member 470. Specifically, in the case of a molded plastic, such as urethane, coordination member 470, the anchor member(s) 478b may be embedded within the coordination member 470. If other materials are used for the coordination member 470, for example, a material that does not permit molding, then the anchor(s) 478b may be received and retained in a suitable recess or cavity formed in the coordination member 470, or otherwise secured to the coordination member 478.

Operation of the artificial foot 10' during walking movement may be described as follows. Beginning with heel strike, the rear flange 226 of the Achilles sheave 220 may absorb impact and protect the rear tension rope 410. The talus body 100 may move downward toward the Achilles sheave 220, with cushioning material (when provided) in the recess 118 of the talus body 100 contacting the top portion 222 of the Achilles sheave 220 to absorb the heel strike. The talus body 100 may rotate (counter-clockwise in FIG. 50) relative to the core 200 during downward movement of the talus body 100, moving the pivot bearings 252 to a bottom of the bearing recesses 132b, 134b of the talus body 100.

The talus body 100 may then rotate about a virtual lateral axis in an opposite direction (clockwise in FIG. 50) relative to the core 200 until the artificial foot reaches a neutral (standing support) position. This rotation may be facilitated by a rebound of the Achilles sheave 220 contacting the cushioning material in the recess 118.

In the neutral position, the pivot bearings 252 may return to a top of the bearing recesses 132b, 134b. Further in this position, the artificial foot may be supported via the bottom of the Achilles sheave 220 and the bottom of the toe bracket 240 as contact/support/load-bearing surfaces.

From the neutral position, tibial progression in a forward direction causes the talus body 100 to rotate about the axle 254 of the first joint 12 via the pivot bearings 252. During a first part of this continued movement, the rear tension rope 410 is tensioned.

With the rear tension rope 410 tensioned, continued tibial progression forward causes heel rise or lift-off. As the heel rises, the artificial foot 10' is supported by the toe bracket 240, with the forward extensions 242 providing a rolling contact surface. During this movement, the talus body 100 and the toe 300 may rotate about their respective lateral axes in opposite directions, which loads the coordination member 470.

In this embodiment, the coordination member 470 may have some elastic properties. Thus, the coordination member 470 may be loaded or tensioned by its connections to the downward extensions 124 of the talus body 100 and its connection to the toe 300 via the tension ropes 478.

Once the limit of the coordination member has been reached, the artificial foot 10' may push off with the toe 300. In particular, the toe 300 may push off in a forward and upward direction, releasing energy stored in the coordination member 470 in that direction as the artificial foot 10' is lifted by the user.

In operation, both embodiments may provide improved movements for an artificial foot device. For example, if the foot encounters an uneven surface, such as a relatively small rock, and a portion of the artificial foot is placed at an angle about its longitudinal axis by such, the limited movement provided in one or both of the joints about the longitudinal axis may allow compliance to avoid translating at least part of the angle to the attachment pylon and/or the user's leg and/or body. In particular, if the uneven surface occurs under the toe bracket and/or the Achilles sheave, the mid-foot joint may permit constrained movement to accommodate the resulting angle. If the uneven surface occurs under the toe, the toe joint may permit constrained movement to accommodate the resulting angle. In either case the other of the two joints may also contribute to accommodation of the resulting angle.

Also, the limited movement provided in one or both of the joints about a substantially vertical axis (e.g., substantially perpendicular to the longitudinal axis) may allow compliance to allow a user to change direction. Although both joints may contribute to the compliance, in some embodiments, the toe joint may provide a primary or sole contribution to the compliance. In some embodiments, the compliance may be provided without substantial energy storage, for example, to avoid undesirable backlash from the change in direction.

It should be understood that the various tension ropes may be of varying degree of flexibility and/or elasticity. Various materials may be employed for the tension ropes, as well as for the discontinuous members of the artificial foot. The materials may be sufficiently rigid, strong, flexible, as appropriate for the function of the particular member. The weight of the user and the selected use by that user may be considered when selecting materials. For example, stronger materials may be required when the user intends to jump and land hard as compared to when the user merely intends to walk. Useful materials for discontinuous members may include metals and/or plastics. Useful materials for tension members may include steel wire rope and aramid fiber ropes. Metal, ceramic and/or plastic bearings may be also useful in the practice of the invention. Preferably, the members of the joints and foot parts of the invention may be made from aluminum (e.g., 7075 T6), steel wire rope, tool steel, plastics and/or other suitable materials based on desired rigidity, flexibility, strength, toughness and the like.

Prototypes of prostheses, orthotics, and robots may be fashioned out of wood, brass, aluminum, plastic, yarn, and steel wire rope. Almost any material having the appropriate characteristics may be used, as long as they do not interfere with the function of the joint or the experience of the user.

The invention may provide artificial tensegrity joints for prosthetic, orthotic, and robotic devices for skeletal animals comprising at least two discontinuous members connected by at least one tension member. The joints of the invention may have a similar range of motion as the equivalent natural joints. Joints provided by the invention include, but may not be limited to foot joints, mid-foot joints and metatarso-phalangeal (MTP) joints. The invention may provide artificial feet and/or foot portions.

In embodiments of the invention, at least one discontinuous member may be artificial. The joint may be a weight-bearing joint. The joint may be for a human. The joint may have similar or better strength as the equivalent natural joint. The joint may be functionally similar to the equivalent natural joint. The joint may be any type of joint for any type of animal, human or non-human.

The invention may provide prosthetic, orthotic, and robotic devices for skeletal animals wherein the device may comprise an artificial tensegrity joint.

The invention may provide devices having one or more artificial tensegrity joints having a range of motion similar to an equivalent natural joint of the animal. Various embodiments may include one or more of any of the aspects set forth herein. The ambulation of the skeletal animal may be improved compared to the animal without the device. The skeletal animal may be physically mature or immature, may include a foot, an ankle, and/or a leg, may include an MTP joint or a midfoot joint, or both, and may be a powered lower body orthotic.

The invention may provide prosthetic for a lower extremity joint of an animal. The device may be of a weight selected to form an artificial foot and/or combined artificial and natural foot that may be substantially equal to the weight of the paired foot of the animal.

The invention may provide a plurality of tensegrity joints for a prosthetic, orthotic, or robotic device for a skeletal animal. Each joint may include at least two discontinuous members connected by at least one tension member.

In an embodiment of the invention, the plurality of tensegrity joints may together form one or more of a foot; foot and ankle; ankle; or a complete leg.

The invention may provide at least a portion of a tensegrity joint for a prosthetic, orthotic, or robotic device for a skeletal animal including at least one artificial discontinuous member connected by at least one tension member, and a means for connecting the tension member to a second artificial or natural discontinuous member.

The invention may provide at least a portion of a tensegrity joint for a prosthetic, orthotic, or robotic device for a skeletal animal including at least one tension member and means for connecting the tension member to two or more artificial or natural discontinuous members.

Various embodiments may include one or more of the following aspects: the heel may be cushioned; the use of an embodiment of the prosthetic foot described herein may improve ambulation of a the human more than one or more of a conventional prosthetic foot (CF), such as a solid ankle cushioned heel foot (SACH), or an energy storing foot (ESF); the use of an embodiment of the device described herein may increase the stride length of the human, which may result in less oxygen consumption by the human and/or decrease the impact force of the heel strike of an intact foot of the human; an embodiment of the device described herein may increase ankle plantarflexion power on toe off compared to a CF or ESF; using an embodiment of the device described herein may ease ambulation, may reduce injuries, or both compared to using a CF or ESF; use of an embodiment of the device described herein may result in a stride that rolls over the prosthetic foot closer to the MTP joint and further from an ankle joint attached to the foot compared to use of a CF or ESF; use of an embodiment of the device described herein may result in about half of the angular change between the lower leg attached to the foot and the floor results from motion at the midfoot joint; use of an embodiment of the device described herein may result in less heel rise before fully dorsiflexing compared to use of a CF or ESF.

The invention may provide a method for ambulating with a prosthetic, orthotic, or robotic foot. The foot may include a midfoot joint or an MTP joint. The method may include bending the foot at the midfoot joint or the MTP joint. The midfoot joint or MTP joint may be a tensegrity joint. The bending the foot at the MTP joint may result in toe off.

The method may including bending the foot at both the midfoot joint and the MTP joint and/or bending the foot at a plurality of MTP joints.

A human may be ambulating. The method may including ambulating with one prosthetic, orthotic, or robotic feet. The method may result in more symmetrical walking than using a CF or an ESF.

The invention may provide a method for ambulating using a prosthetic, orthotic, or robotic foot. The method may include performing a toe off step.

The invention may provide a method for ambulating including bending a prosthetic, orthotic, or robotic joint. The joint may include one or more of an MTP joint and a mid-foot joint.

The method may include one or more of: bending a prosthetic, orthotic, or robotic mid-foot joint; and bending a prosthetic, orthotic, or robotic MTP joint.

The invention may provide a method of bending a prosthetic, orthotic, or robotic joint comprising one or more of the following aspects: applying force to a first structural member; applying tension to a tension member; and thereby applying a force to a second structural member.

Various embodiments may include two or more universal joints.

While certain exemplary embodiments have been described above in detail and shown in the accompanying drawings, it is to be understood that such embodiments are merely illustrative of and not restrictive of the broad invention.

In particular, it should be recognized that the teachings provided herein apply to a wide variety of systems and processes. It will thus be recognized that various modifications may be made to the illustrated and other embodiments described herein, without departing from the broad inventive scope thereof. In view of the above it will be understood that the invention is not limited to the particular embodiments or arrangements disclosed, but is rather intended to cover any changes, adaptations or modifications which are within the scope and spirit of the disclosure provided herein.

What is claimed is:

1. An artificial foot comprising
   a core;
      an axle that extends laterally from opposing sides of the core;
      a talus body operatively coupled with the core at a first joint that provides for constrained relative movement between the talus body and the core; and
      a pair of pivot bearings having bearing surfaces; wherein
      the pivot bearings pivot on respective opposing ends of the axle;
      the talus body further defines a pair of opposing bearing recesses that interfaces with the bearing surfaces;
      the first joint includes the interfaces between the bearing surfaces and bearing recesses; and
      the bearing surfaces and bearing recesses bear compressive and frictional forces when the core interfaces with the talus body under a load during walking movement;
      wherein the first joint includes at least a first tension member coupling the talus body and the core.

2. The artificial foot of claim 1, wherein the core comprises a core assembly including a core body and an Achilles sheave coupled with the core body.

3. The artificial foot of claim 1, wherein the first joint includes a second tension member coupling the talus body and the core, the first tension member constraining relative movement of the talus body and the core in at least a first direction, the second tension member constraining relative movement of the talus body and the core in at least a second direction different from the first direction.

4. The artificial foot of claim 1, wherein
   the talus body and the core define a longitudinal axis of the artificial foot;
   a lateral axis is defined normal to the longitudinal axis in a horizontal plane; and
   the first joint permits limited relative rotation of the talus body and the core about the lateral axis.

5. The artificial foot of claim 1, wherein
   the talus body and the core define a longitudinal axis of the artificial foot; and
   the first joint permits limited relative rotation of the talus body and the core about the longitudinal axis.

6. The artificial foot of claim 1, wherein
   the talus body and the core define a longitudinal axis of the artificial foot;
   a vertical axis is defined normal to the longitudinal axis in a vertical plane; and
   the first joint permits limited relative rotation of the talus body and the core about the vertical axis.

7. The artificial foot of claim 1, wherein the first joint includes a constraint structure that limits relative movement between the talus body and the core other than about a lateral axis.

8. The artificial foot of claim 7, wherein the constraint structure is configured to constrain relative movement between the talus body and the core about a longitudinal axis.

9. The artificial foot of claim 7, wherein the constraint structure is configured to constrain relative movement between the talus body and the core about a substantially vertical axis.

10. The artificial foot of claim 1, further comprising
    a mid-foot bearing that is operatively coupled to the talus body by the at least one tension member.

11. The artificial foot of claim 1, wherein the constrained relative movement between the talus body and the core substantially corresponds to a coordinated movement of a first natural joint and a second natural joint during ambulation of a natural human foot.

12. The artificial foot of claim 1, wherein the first joint includes a constraint structure that interfaces with the pair of pivot bearings and thereby positively limits a range of motion of the first joint in either a lateral direction, a twisting direction, a vertical direction, or any combination thereof.

13. The artificial foot of claim 1, wherein each of opposing bearing recesses is slightly larger, deeper, or both, than a size, extension, or both, of the respective bearing surfaces of the pivot bearings and thereby allow for play in a longitudinal direction, a lateral direction, a vertical direction, or a combination thereof, between the bearing recesses and the bearing surfaces of the pivot bearings.

14. The artificial foot of claim 1, wherein the axle is configured to rotate with respect to the core.

15. The artificial foot of claim 1, wherein the axle is fixed with respect to the core.

16. The artificial foot of claim 1 further comprising a toe operatively coupled with the core by a second joint that provides for constrained relative movement between the core and the toe.

17. The artificial foot of claim 16, wherein the second joint includes at least a first tension member coupling the core and the toe.

18. The artificial foot of claim 17, wherein the second joint includes a second tension member coupling the core and the toe, the first tension member constraining relative movement of the core and the toe in at least a first direction, the second tension member constraining relative movement of the core and the toe in at least a second direction different from the first direction.

19. The artificial foot of claim 16, wherein
    the talus body, the core, and the toe define a longitudinal axis of the artificial foot;
    a lateral axis is defined normal to the longitudinal axis in a horizontal plane; and
    the second joint permits limited relative rotation of the toe and the core about the lateral axis.

20. The artificial foot of claim 16, wherein
    the talus body, the core, and the toe define a longitudinal axis of the artificial foot; and
    the second joint permits limited relative rotation of the toe and the core about the longitudinal axis.

21. The artificial foot of claim 16, wherein
    the talus body, the core, and the toe define a longitudinal axis of the artificial foot;
    a vertical axis is defined normal to the longitudinal axis in a vertical plane; and
    the second joint permits limited relative rotation of the toe and the core about the vertical axis.

22. The artificial foot of claim 16, wherein the second joint includes a constraint structure that limits relative movement between the core and the toe other than about a lateral axis.

23. The artificial foot of claim 22, wherein the constraint structure is configured to constrain relative movement between the core and the toe about a longitudinal axis.

24. The artificial foot of claim 22, wherein the constraint structure is configured to constrain relative movement between the core and the toe about a substantially vertical axis.

25. The artificial foot of claim 22, wherein the constraint structure comprises a toe race.

26. The artificial foot of claim 25, wherein the toe race is operatively coupled with the core and the toe and configured to engage a respective feature of the core and the toe to constrain relative movement between the core and the toe.

27. The artificial foot of claim 25, wherein the toe race is operatively coupled with the core and the toe by at least one tension member.

28. The artificial foot of claim 16, wherein
the constrained relative movement between the talus body and the core substantially corresponds to a coordinated movement of a first natural joint and a second natural joint during ambulation of a natural human foot; and
the constrained relative movement between the core and the toe substantially corresponds to a coordinated movement of a third natural joint, different from the first and second natural joints, during ambulation of a natural human foot.

29. The artificial foot of claim 16, further comprising a coordination member operatively coupled with the talus body and the toe, the coordination member configured to store and release energy during a walking movement of the artificial foot.

30. The artificial foot of claim 16, further comprising at least one member operatively coupled with the core and the toe, the at least one member configured to store and release energy during a walking movement of the artificial foot.

31. The artificial foot of claim 16, wherein the second joint is a tensegrity joint.

32. The artificial foot of claim 16, wherein the second joint includes a constraint structure that positively limits a range of motion of the second joint.

33. The artificial foot of claim 16, wherein the core comprises a core assembly including a core body, an Achilles sheave coupled with the core body, and a toe bracket coupled with the core body, the toe bracket operatively coupled with the toe.

34. An artificial foot comprising
a core;
an axle that extends laterally from opposing sides of the core;
a talus body operatively coupled with the core at a first joint that provides for constrained relative movement between the talus body and the core; and
a pair of pivot bearings having bearing surfaces; wherein
the pivot bearings pivot on respective opposing ends of the axle;
the talus body further defines a pair of opposing bearing recesses that interfaces with the bearing surfaces;
the first joint includes the interfaces between the bearing surfaces and bearing recesses; and
the bearing surfaces and bearing recesses bear compressive and frictional forces when the core interfaces with the talus body under a load during walking movement;
the core comprises a core assembly including a core body and an Achilles sheave coupled with the core body.

* * * * *